US 10,857,076 B2

(12) United States Patent
Boswell et al.

(10) Patent No.: US 10,857,076 B2
(45) Date of Patent: *Dec. 8, 2020

(54) BARRIER PATCH WITH SOLUBLE FILM AND METHODS OF IMPROVING SKIN APPEARANCE

(71) Applicant: The Procter & Gamble Company, Cincinnati, OH (US)

(72) Inventors: Emily Charlotte Boswell, Cincinnati, OH (US); Jack Alan Hunter, Springboro, OH (US); Michael Joseph Roddy, Cincinnati, OH (US); Elizabeth Anne Wilder, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 332 days.

This patent is subject to a terminal disclaimer.

(21) Appl. No.: 15/843,866

(22) Filed: Dec. 15, 2017

(65) Prior Publication Data

US 2018/0360698 A1 Dec. 20, 2018

Related U.S. Application Data

(60) Provisional application No. 62/444,058, filed on Jan. 9, 2017.

(51) Int. Cl.
| | |
|---|---|
| *A61K 8/81* | (2006.01) |
| *A61K 8/87* | (2006.01) |
| *A61K 8/88* | (2006.01) |
| *A61K 8/89* | (2006.01) |
| *A61K 9/70* | (2006.01) |

(Continued)

(52) U.S. Cl.
CPC ............ *A61K 8/0208* (2013.01); *A45D 37/00* (2013.01); *A45D 44/002* (2013.01); *A61K 8/02* (2013.01); *A61K 9/7084* (2013.01); *A61K 31/455* (2013.01); *A61K 47/02* (2013.01); *A61K 47/10* (2013.01); *A61K 47/183* (2013.01);

(Continued)

(58) Field of Classification Search
None
See application file for complete search history.

(56) References Cited

U.S. PATENT DOCUMENTS

| | | |
|---|---|---|
| 3,155,034 A | 11/1964 | Reinke |
| 3,482,300 A | 12/1969 | Reinke |

(Continued)

FOREIGN PATENT DOCUMENTS

| | | |
|---|---|---|
| EP | 0238200 A2 | 9/1987 |
| EP | 0904049 B1 | 6/2001 |

(Continued)

OTHER PUBLICATIONS

All Office Actions, U.S. Appl. No. 15/843,812.

(Continued)

*Primary Examiner* — Kyung S Chang
(74) *Attorney, Agent, or Firm* — John G. Powell

(57) ABSTRACT

A multilayer beauty care product or method is provided. The beauty care product has a water soluble film zone that includes a water soluble film forming polymer and a cosmetic composition with an effective amount of a skin active agent. The product also has a barrier patch having a backing layer and a pressure sensitive adhesive zone. The adhesive zone and the water soluble film zone are continuous, discontinuous, or a combination thereof. The product exhibits a dynamic modulus.

24 Claims, 5 Drawing Sheets

(51) Int. Cl.
  *A61Q 19/00* (2006.01)
  *A61K 8/02* (2006.01)
  *A45D 44/00* (2006.01)
  *A45D 37/00* (2006.01)
  *A61K 31/455* (2006.01)
  *A61K 47/02* (2006.01)
  *A61K 47/10* (2017.01)
  *A61K 47/18* (2017.01)
  *A61K 47/26* (2006.01)
  *A61K 47/32* (2006.01)

(52) U.S. Cl.
  CPC .............. *A61K 47/26* (2013.01); *A61K 47/32* (2013.01); *A61Q 19/00* (2013.01); *A45D 2200/1036* (2013.01)

(56) References Cited

U.S. PATENT DOCUMENTS

| | | |
|---|---|---|
| 3,696,741 A | 10/1972 | Reinke |
| 3,759,799 A | 9/1973 | Reinke |
| 3,759,800 A | 9/1973 | Reinke |
| 4,341,209 A | 7/1982 | Schaar |
| 4,377,616 A | 3/1983 | Ashcraft et al. |
| 4,472,328 A | 9/1984 | Sugimoto et al. |
| 4,519,538 A | 5/1985 | Omichi |
| 4,578,297 A | 3/1986 | Duncan |
| 4,649,186 A | 3/1987 | Jenkins et al. |
| 4,699,792 A | 10/1987 | Nick et al. |
| 4,711,781 A | 12/1987 | Nick et al. |
| 4,725,439 A | 2/1988 | Campbell et al. |
| 4,743,249 A | 5/1988 | Loveland |
| 4,773,408 A | 9/1988 | Cilento et al. |
| 4,781,294 A | 11/1988 | Croce |
| 5,051,259 A | 9/1991 | Olsen et al. |
| 5,123,900 A | 6/1992 | Wick |
| 5,132,115 A | 7/1992 | Wolter et al. |
| 5,180,626 A | 1/1993 | Ishibashi et al. |
| 5,262,165 A | 11/1993 | Govil et al. |
| 5,387,450 A | 2/1995 | Stewart |
| 5,455,043 A | 10/1995 | Fischel-Ghodsian |
| 5,476,664 A | 12/1995 | Robinson et al. |
| 5,503,844 A | 4/1996 | Kwiatek et al. |
| 5,559,165 A | 9/1996 | Paul |
| 5,628,737 A | 5/1997 | Dobrin et al. |
| 5,629,014 A | 5/1997 | Kwiatek et al. |
| 5,641,506 A | 6/1997 | Talke et al. |
| 5,713,842 A | 2/1998 | Kay |
| 5,723,138 A | 3/1998 | Bae et al. |
| 5,785,978 A | 7/1998 | Porter et al. |
| 5,820,877 A | 10/1998 | Yamaguchi et al. |
| 5,958,447 A | 9/1999 | Haralambopoulos et al. |
| 5,965,154 A | 10/1999 | Haralambopoulos |
| 5,968,533 A | 10/1999 | Porter et al. |
| 6,162,458 A | 12/2000 | Asada et al. |
| 6,168,028 B1 | 1/2001 | Telesca et al. |
| 6,183,770 B1 | 2/2001 | Muchin et al. |
| 6,200,596 B1 | 3/2001 | Schwartzmiller et al. |
| D440,315 S | 4/2001 | Hassenbein et al. |
| 6,221,369 B1 | 4/2001 | Pool et al. |
| 6,277,401 B1 | 8/2001 | Bello et al. |
| 6,325,565 B1 | 12/2001 | Girardot et al. |
| 6,338,855 B1 | 1/2002 | Albacarys et al. |
| 6,448,303 B1 | 9/2002 | Paul |
| 6,495,158 B1 | 12/2002 | Buseman et al. |
| 6,495,229 B1 | 12/2002 | Carte et al. |
| 6,593,602 B2 | 7/2003 | Liang et al. |
| D484,985 S | 1/2004 | Takizawa et al. |
| 6,673,363 B2 | 1/2004 | Luo et al. |
| 6,676,962 B1 | 1/2004 | Muller |
| 6,730,317 B2 | 5/2004 | Gueret |
| 6,899,840 B2 | 5/2005 | Ueda et al. |
| 6,926,960 B1 | 8/2005 | Hoshino et al. |
| 6,953,602 B2 | 10/2005 | Carte et al. |
| D519,239 S | 4/2006 | Katagiri |
| 7,063,859 B1 | 6/2006 | Kanios et al. |
| 7,256,234 B2 | 8/2007 | Nierle et al. |
| 7,531,185 B2 | 5/2009 | Chen et al. |
| 7,658,942 B2 | 2/2010 | Deckner et al. |
| 7,854,938 B2 | 12/2010 | Ueda et al. |
| 8,066,117 B2 | 11/2011 | Ueda et al. |
| 8,173,233 B2 | 5/2012 | Rogers et al. |
| 8,353,399 B2 | 1/2013 | Ueda et al. |
| 8,512,837 B2 | 8/2013 | Barreneche |
| 8,728,514 B2 | 5/2014 | Choi et al. |
| 9,066,888 B2 | 6/2015 | Kugelmann et al. |
| 2002/0022052 A1 | 2/2002 | Dransfield |
| 2002/0077266 A1 | 6/2002 | Gabriel et al. |
| 2002/0187181 A1 | 12/2002 | Godbey et al. |
| 2003/0072724 A1 | 4/2003 | Maibach et al. |
| 2003/0082219 A1 | 5/2003 | Warren et al. |
| 2003/0152610 A1 | 8/2003 | Rolf et al. |
| 2003/0167556 A1 | 9/2003 | Kelley |
| 2003/0175328 A1 | 9/2003 | Shefer et al. |
| 2003/0180347 A1 | 9/2003 | Young et al. |
| 2004/0009202 A1 | 1/2004 | Woller |
| 2004/0116018 A1 | 6/2004 | Fenwick et al. |
| 2004/0202706 A1 | 10/2004 | Koo et al. |
| 2005/0013784 A1 | 1/2005 | Trigg et al. |
| 2005/0266059 A1 | 12/2005 | Poss |
| 2006/0104931 A1 | 5/2006 | Fukutome et al. |
| 2006/0121097 A1 | 6/2006 | Lodge et al. |
| 2006/0177487 A1 | 8/2006 | Martz |
| 2006/0198879 A1 | 9/2006 | Fukuta et al. |
| 2007/0020220 A1 | 1/2007 | Osborne |
| 2007/0060855 A1 | 3/2007 | Leung et al. |
| 2007/0254021 A1 | 11/2007 | Scimeca et al. |
| 2007/0259029 A1 | 11/2007 | McEntire et al. |
| 2007/0292491 A1 | 12/2007 | Hansen et al. |
| 2007/0298089 A1 | 12/2007 | Saeki et al. |
| 2008/0014231 A1 | 1/2008 | Okano |
| 2008/0138593 A1 | 6/2008 | Martinez |
| 2008/0260808 A1 | 10/2008 | Pinna et al. |
| 2009/0010998 A1 | 1/2009 | Marchitto et al. |
| 2009/0155326 A1 | 6/2009 | Mack et al. |
| 2009/0234308 A1 | 9/2009 | Jackson et al. |
| 2009/0249558 A1 | 10/2009 | Fileccia et al. |
| 2009/0258062 A1 | 10/2009 | Horstmann |
| 2009/0263600 A1 | 10/2009 | Miyashita et al. |
| 2009/0317578 A1 | 12/2009 | Rogers et al. |
| 2009/0317605 A1 | 12/2009 | Rogers et al. |
| 2010/0239619 A1 | 9/2010 | Hurwitz |
| 2011/0200652 A1 | 8/2011 | Smith et al. |
| 2011/0300198 A1 | 12/2011 | Nussinovitch et al. |
| 2012/0308619 A1 | 12/2012 | Tousley |
| 2013/0042417 A1 | 2/2013 | Smith et al. |
| 2013/0178407 A1 | 7/2013 | Fileccia et al. |
| 2014/0079938 A1 | 3/2014 | Perick et al. |
| 2014/0083878 A1 | 3/2014 | Tang et al. |
| 2014/0276478 A1 | 9/2014 | Liao et al. |
| 2014/0376835 A1 | 12/2014 | Rogers et al. |
| 2014/0377512 A1 | 12/2014 | Rogers et al. |
| 2015/0209243 A1 | 7/2015 | Shiroya et al. |
| 2015/0307264 A1 | 10/2015 | Boswell et al. |
| 2015/0320606 A1 | 11/2015 | Kawahara |
| 2016/0107004 A1 | 4/2016 | Wilder et al. |
| 2017/0042311 A1 | 2/2017 | Wilder et al. |
| 2017/0112724 A1 | 4/2017 | Boswell et al. |
| 2017/0112725 A1 | 4/2017 | Boswell et al. |
| 2017/0112726 A1 | 4/2017 | Boswell et al. |
| 2017/0112727 A1 | 4/2017 | Boswell et al. |
| 2018/0098921 A1 | 4/2018 | Boswell et al. |
| 2018/0193229 A1 | 7/2018 | Boswell et al. |
| 2018/0193230 A1 | 7/2018 | Boswell et al. |
| 2018/0200158 A1 | 7/2018 | Boswell et al. |
| 2018/0369079 A1 | 12/2018 | Boswell |
| 2019/0282459 A1 | 9/2019 | Boswell |

FOREIGN PATENT DOCUMENTS

| | | |
|---|---|---|
| EP | 2316436 A1 | 5/2011 |
| EP | 2316438 A1 | 5/2011 |
| EP | 2559425 A1 | 2/2013 |
| GB | 2221620 B | 9/1991 |

(56) References Cited

FOREIGN PATENT DOCUMENTS

| | | |
|---|---|---|
| JP | S5052044 U | 5/1975 |
| JP | 2002249422 A | 9/2002 |
| JP | 2004051516 A | 2/2004 |
| JP | 2006021789 | 1/2006 |
| JP | 2011178693 | 2/2010 |
| KR | 20080014461 A | 2/2008 |
| KR | 100871282 B1 | 11/2008 |
| WO | WO9216202 A1 | 10/1992 |
| WO | WO9528136 A1 | 10/1995 |
| WO | WO1996014822 | 5/1996 |
| WO | WO97032567 A1 | 9/1997 |
| WO | WO9748387 A1 | 12/1997 |
| WO | WO9926572 A1 | 6/1999 |
| WO | WO2000030694 | 6/2000 |
| WO | WO0075220 A1 | 12/2000 |
| WO | WO2001001816 | 1/2001 |
| WO | WO2001001951 | 1/2001 |
| WO | WO2001001952 | 1/2001 |
| WO | WO2001078678 | 10/2001 |
| WO | WO03063817 A1 | 8/2003 |
| WO | WO03084579 A1 | 10/2003 |
| WO | WO2004077990 A1 | 9/2004 |
| WO | WO2004078122 A2 | 9/2004 |
| WO | WO2006062740 A3 | 8/2006 |
| WO | WO2008071310 A1 | 6/2008 |
| WO | WO2009055048 A1 | 4/2009 |
| WO | WO2010057189 A1 | 5/2010 |
| WO | WO2014079459 A1 | 5/2014 |

OTHER PUBLICATIONS

All Office Actions, U.S. Appl. No. 15/843,866.
All Office Actions, U.S. Appl. No. 15/865,384.
All Office Actions, U.S. Appl. No. 15/865,402.
Ovington, Liza G., Advances in Wound Dressings, Clinics in Dermatology, 2007, vol. 25, pp. 33-38.
All Office Actions, U.S. Appl. No. 14/919,048.
All Office Actions, U.S. Appl. No. 16/015,644.
All Office Actions, U.S. Appl. No. 16/358,225.
All Office Actions, U.S. Appl. No. 14/918,989.
All Office Actions, U.S. Appl. No. 15/296,630.
All Office Actions, U.S. Appl. No. 15/296,713.
All Office Actions, U.S. Appl. No. 15/296,736.
All Office Actions, U.S. Appl. No. 15/839,287.
All Office Actions, U.S. Appl. No. 15/296,768.
How to Make Water-in-Oil (W/O) Emulsions, Making Cosmetics Inc., http://www.makingcosmetics.com/articles/27-how-to-make-water-in-oil-emulsions.pdf, retrieved online on Mar. 20, 2014.
International Search Report and Written Opinion of the International Searching Authority, PCT/US019/022838, dated Jun. 26, 2019, 11 pages.
International Search Report and Written Opinion of the International Searching Authority, PCT/US2015/056667, dated Dec. 21, 2015, 13 pages.
International Search Report and Written Opinion of the International Searching Authority, PCT/US2015/056670, dated Dec. 21, 2015, 16 pages.
International Search Report and Written Opinion of the International Searching Authority, PCT/US2016/057470, dated Dec. 20, 2016, 10 pages.
International Search Report and Written Opinion of the International Searching Authority, PCT/US2016/057472, dated Dec. 23, 2016, 12 pages.
International Search Report and Written Opinion of the International Searching Authority, PCT/US2016/057476, dated Dec. 20, 2016, 10 pages.
International Search Report and Written Opinion of the International Searching Authority, PCT/US2018/038896, dated Oct. 5, 2018, 10 pages.
PCT International Search Report, dated Dec. 30, 2016, 10 pages.
Schut, J., Foamed Films Find New Niches, Plastics Technology, Jan. 2002 Issue, 5 pages.
www.gnpd.com Record ID: 1119887, Day Out First Aid Kit, Savlon, Jun. 2009.
U.S. Appl. No. 15/865,384, filed Jan. 9, 2018, Boswell et al.
U.S. Appl. No. 15/865,402, filed Jan. 9, 2018, Boswell et al.
U.S. Appl. No. 15/843,812, filed Dec. 15, 2017, Boswell et al.
U.S. Appl. No. 15/843,866, filed Dec. 15, 2017, Boswell et al.
International Search Report and Written Opinion of the International Searching Authority, PCT/US2018/012869, dated Apr. 30, 2018, 12 pages.
International Search Report and Written Opinion of the International Searching Authority, PCT/US2018/012870, dated Apr. 30, 2018, 13 pages.
International Search Report and Written Opinion of the International Searching Authority, PCT/US2018/012871, dated May 28, 2018, 10 pages.
International Search Report and Written Opinion of the International Searching Authority, PCT/US2018/012873, dated May 28, 2018, 10 pages.

BARRIER PATCH WITH SOLUBLE FILM AND METHODS OF IMPROVING SKIN APPEARANCE

TECHNICAL FIELD

The present invention relates to products comprising a barrier patch and soluble film zones comprising skin active agents for improving skin appearance. The present invention also relates to a method of delivering cosmetic compositions to a target area of the skin via the use of such product.

BACKGROUND OF THE INVENTION

The benefits of using a patch or mask device comprising skin agents to cosmetically treat the skin, have been recognized in the art. A variety of cosmetic patches or devices are commercially marketed or described as being useful for the delivery of skin actives. Patches have also been described in the literature and marketed in the medical field as a useful means for the transdermal administration of drugs.

However, many patches or devices suffer drawbacks which include ineffective release of the active ingredients to the skin. Other patches are dry, rough, and inflexible and thus are tight and uncomfortable to wear. Many existing cosmetic patches typically comprise flat two dimensional substrates. These substrates remain in this inflexible configuration during wear and do not conform well to three dimensional surfaces of the skin. Existing patches are not able to conform as the facial skin flexes and changes during movement and changing facial expressions. Thus in this dynamic environment, these patches often do not conform well to the contours of the skin surface to which they are applied. Gaps between the skin surface and the patch may form or the patch may simply be uncomfortable to wear especially for long periods of time. Thus many patches have undesirable in-use characteristics.

Certain beauty care patch systems comprise an active contained in a reservoir in which the active is present in solid, liquid or dissolved form. These systems may also have a layer of pressure-sensitive adhesive by which the system can be brought into close contact with the skin. These systems are limited when the active does not diffuse through the reservoir or adhesive layer, when a chemical reaction occurs between the active and the reservoir material or adhesive, or when the active is insoluble or only poorly soluble in the reservoir or adhesive.

Thus an improved multilayered beauty care product is provided. The product comprises a soluble film zone containing the active agent and a water soluble film forming polymer. As the soluble film forming polymer dissolves, the active is released. The soluble film zone or polymer or product provides a dynamic modulus wherein the modulus decreases during use of the product to improve the comfort and conformability around the curved surfaces of the skin, even in a low water environment. Thus the comfort of the product improves during wear. The product also comprises a pressure sensitive adhesive that is substantially separate from the active ingredients so that any interaction between the two is minimized.

SUMMARY OF THE INVENTION

The present invention solves at least one of these problems by incorporating at least one soluble film zone into a beauty care product and the soluble film is directed, in part, to having the appropriate degree of modulus upon hydration and/or solubility in water.

In one aspect a multi-layered beauty care product for applying a skin active agent to the skin, is provided comprising:
a barrier patch comprising:
   a backing layer having a first surface and a second surface; a WVTR from about 1 $g/m^2/24$ h to about 500 $g/m^2/24$ h, preferably from about 1 $g/m^2/24$ h to about 250 $g/m^2/24$ h, more preferably from about 2 $g/m^2/24$ h to about 20 $g/m^2/24$ h;
   a pressure sensitive adhesive zone, having a upper surface and a lower surface, the lower surface of the pressure sensitive adhesive zone in contact with the first surface of the backing layer;
a water soluble film zone comprising:
   a water soluble film forming polymer;
   a cosmetic composition comprising an effective amount of a skin active agent;
   the soluble film zone is in contact with either the first surface of the backing layer, the upper surface of the adhesive zone, or both;
wherein the water soluble film zone has an initial modulus, preferably in the dry state, of from about 30 MPa to about 600 MPa, preferably from about 75 MPa to about 500 MPa, more preferably from about 100 MPa to about 450 MPa; and the water soluble film zone or product is capable of a % weight increase, preferably at 1 hour, or 6 hours or 24 hours, from about 10% to about 80%, preferably from about 20% to about 80%.

In another aspect, a method of improving the appearance of skin is provided, comprising the steps of:
a. identifying a target portion of skin, preferably facial skin surface, in need of improvement;
b. topically applying, to the target portion of skin, a multi-layered beauty care product comprising:
   a barrier patch comprising:
      a backing layer having a first surface and a second surface; a WVTR from about 1 $g/m^2/24$ h to about 500 $g/m^2/24$ h, preferably from about 1 $g/m^2/24$ h to about 250 $g/m^2/24$ h, more preferably from about 2 $g/m^2/24$ h to about 20 $g/m^2/24$ h;
      a pressure sensitive adhesive zone, having a upper surface and a lower surface, the lower surface of the pressure sensitive adhesive zone in contact with the first surface of the backing layer;
   a water soluble film zone comprising:
      a water soluble film forming polymer;
      a cosmetic composition comprising an effective amount of a skin active agent;
      the soluble film zone is in contact with either the first surface of the
      backing layer, the upper surface of the adhesive zone, or both;
   wherein the water soluble film zone has an initial modulus, preferably in the dry state, of from about 30 MPa to about 600 MPa, preferably from about 75 MPa to about 500 MPa, more preferably from about 100 MPa to about 450 MPa; and
wherein the product is applied for a treatment period.

In an aspect the treatment period is a sufficient time for the product to improve the appearance of the skin. In an aspect the target portion of skin is healthy skin. In an aspect the pressure sensitive adhesive zone is continuous and the water soluble film zone may be continuous or discontinuous. The beauty care product may be applied to any keratinous tissue.

BRIEF DESCRIPTION OF THE DRAWINGS

While the specification concludes with claims that particularly point out and distinctly claim the invention, it is believed that the present invention will be better understood from the following description of aspects, taken in conjunction with the accompanying drawings in which:

DETAILED DESCRIPTION OF THE INVENTION

Figure 1:
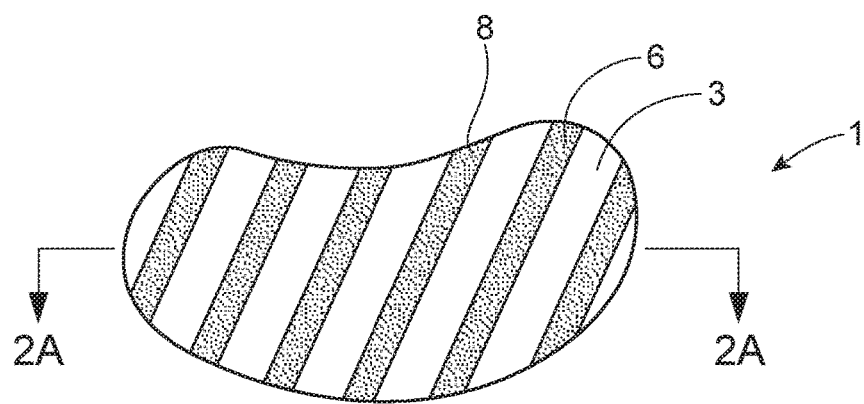
FIG. 1 is a top plan view of a beauty care product comprising discontinuous water soluble film zones and a continuous adhesive zone, as shown and described herein.

While the specification concludes with the claims particularly pointing out and distinctly claiming the invention, it is believed that the present invention will be better understood from the following description.

All percentages and ratios used herein are by weight of the total composition. All numeric ranges are inclusive of narrower ranges; delineated upper and lower range limits are interchangeable to create further ranges not explicitly delineated. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

As used herein, "molecular weight" or "Molecular weight" refers to the weight average molecular weight unless otherwise stated. Molecular weight is measured using industry standard method, gel permeation chromatography ("GPC").

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions onto a substrate such as the human skin surface or epidermis.

The term "dermatologically acceptable," as used herein, means that the compositions or components thereof so described are suitable for use in contact with mammalian keratinous tissue without undue toxicity, incompatibility, instability, allergic response, and the like.

The term "facial skin surface" as used herein refers to one or more of forehead, periorbital, cheek, perioral, chin, and nose skin surfaces. While facial skin surfaces are of concern and are exemplified herein, other skin surfaces may be treated with the compositions and methods of the present invention, for example, surfaces typically not covered by clothing such as facial skin surfaces, hand and arm skin surfaces, foot and leg skin surfaces, and neck and chest skin surfaces (e.g., décolletage).

As used herein "healthy skin" means that the physical barrier function of the epidermis and the dermis is maintained intact for example, the stratum corneum of skin is intact, and is not physically disrupted, removed, subject to reduction, wounded, altered or ablated using mechanical, optical, or thermal means.

The term "keratinous tissue," as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The terms "topical application", "topically", and "topical", as used herein, mean to apply (e.g., spread, spray) the compositions of the present invention onto the surface of the keratinous tissue.

As used herein, "effective amount" means an amount of a compound or composition sufficient to significantly induce a positive keratinous tissue benefit, including independently or in combination with other benefits disclosed herein. This means that the content and/or concentration of agent in the formulation is sufficient that when the formulation is applied with normal frequency and in a normal amount, the formulation can result in the treatment of one or more undesired keratinous tissue conditions (e.g., skin wrinkles). For instance, the amount can be an amount sufficient to inhibit or enhance some biochemical function occurring within the keratinous tissue. This amount of the skin care agent may vary depending upon the type of product, the type of keratinous tissue condition to be addressed, and the like.

The term "safe and effective amount" as used herein means an amount of a compound or composition sufficient to significantly induce a positive benefit, preferably a positive keratinous tissue appearance, including independently or in combinations with the benefits disclosed herein, but low enough to avoid serious side effects, i.e., to provide a reasonable benefit to risk ratio, within the scope of sound judgment of the skilled artisan.

As used herein, the term "water impermeable" includes materials or objects through which water in its liquid state does not pass.

The term "substantially free of" refers to an amount of a material that is less than 2%, 1%, 0.5%, 0.25%, 0.1%, 0.05%, 0.01%, or 0.001% by weight, of product, the barrier patch, the water soluble film zone, the water soluble film forming polymer, or the backing layer of the barrier patch. "Free of" refers to no detectable amount of the stated ingredient or thing.

"Bio-based content" refers to the amount of carbon from a renewable resource in a material as a percent of the mass of the total organic carbon in the material, as determined by ASTM D6866-10, Method B. Note that any carbon from inorganic sources such as calcium carbonate is not included in determining the bio-based content of the material.

"Biodegradation" refers to a process of chemical dissolution of materials by microorganisms or other biological means.

"Bio-identical polymer" refers to polymers that are made from monomers where at least one monomer is derived from renewable resources. For instance, a bio-identical polyolefin is made from olefins that are derived from renewable resources, whereas a petro-based polyolefin is made from olefins typically derived from non renewable oil or gas.

"Bio-new polymer" refers to polymers that are directly derived (i.e., no intermediate compound in the derivation process) from renewable resources. Such renewable resources include cellulose (e.g. pulp fibers), starch, chitin, polypeptides, poly(lactic acid), polyhydroxyalkanoates, and the like.

"Monomeric compound" refers to an intermediate compound that may be polymerized to yield a polymer.

As used herein, the term "nonwoven" means a porous, fibrous material made from continuous (long) filaments (fibers) and/or discontinuous (short) filaments (fibers) by processes such as, for example, spunbonding, meltblowing, carding, and the like. Nonwoven webs do not have a woven or knitted filament pattern.

"Petrochemical" refers to an organic compound derived from petroleum, natural gas, or coal.

"Petroleum" refers to crude oil and its components of paraffinic, cycloparaffinic, and aromatic hydrocarbons. Crude oil may be obtained from tar sands, bitumen fields, and oil shale.

"Polymers derived directly from renewable resources" refer to polymers obtained from a renewable resource without intermediates. Typically, these types of polymers would tend be "bio-new".

"Post-consumer recycled polymers" refer to synthetic polymers recovered after consumer usage and includes recycled polymers from plastic bottles (e.g., laundry, milk, and soda bottles).

"Renewable resource" refers to a natural resource that can be replenished within a 100 year time frame. The resource may be replenished naturally, or via agricultural techniques. Renewable resources include plants, animals, fish, bugs, insects, bacteria, fungi, and forestry products. They may be naturally occurring, hybrids, or genetically engineered organisms. Natural resources such as crude oil, coal, and peat which take longer than 100 years to form are not considered to be renewable resources.

Water Soluble Film Zone

The water soluble film zone comprises a water soluble film forming polymer and a cosmetic composition comprising an effective amount of a skin active agent. The water soluble film forming polymer forms a water soluble film. As used herein "water-soluble film" means a film that dissolves according to the dissolution method herein.

In an aspect the water soluble film zone comprises from about 30% to about 99% or from about 40% to about 90%, more preferably from about 50% to about 75% of a water soluble film forming polymer.

As used herein a "low water environment" of the skin, means the humidity or moisture provided, under occlusion, from the inner skin layer(s) of healthy skin to the surface of the skin via the pores in the skin. This may comprise components of sweat, sebum or oil. For example a low water environment includes the humidity build up on the skin when the product herein is applied to the skin for about 1 to 8 hours or longer, the product comprising a backing layer having a low breathability (e.g. low WVTR, the proper thickness, etc.), as provided herein.

The water soluble film zone or product is thus capable of increasing in weight as the buildup of water/humidity occurs under the product when applied to the skin. In an aspect, the water soluble film zone, water soluble film, or product is capable of a % weight increase, at 1 hour, 6 hours, and/or 24 hours, from about 10% to about 80%, or from about 20% to about 80%, or from about 20% to about 70%, or from about 20% to about 60% or from about 25% to about 50%, according to the Percentage Weight Gain Method herein. As this transformation occurs, the skin active agent may be released from the product to the skin of the user and be absorbed into the skin to have the intended effect. To approximate the change in weight for the water soluble film zone, the water soluble film made from the water soluble film forming polymer may also be used in the method.

Figure 7:
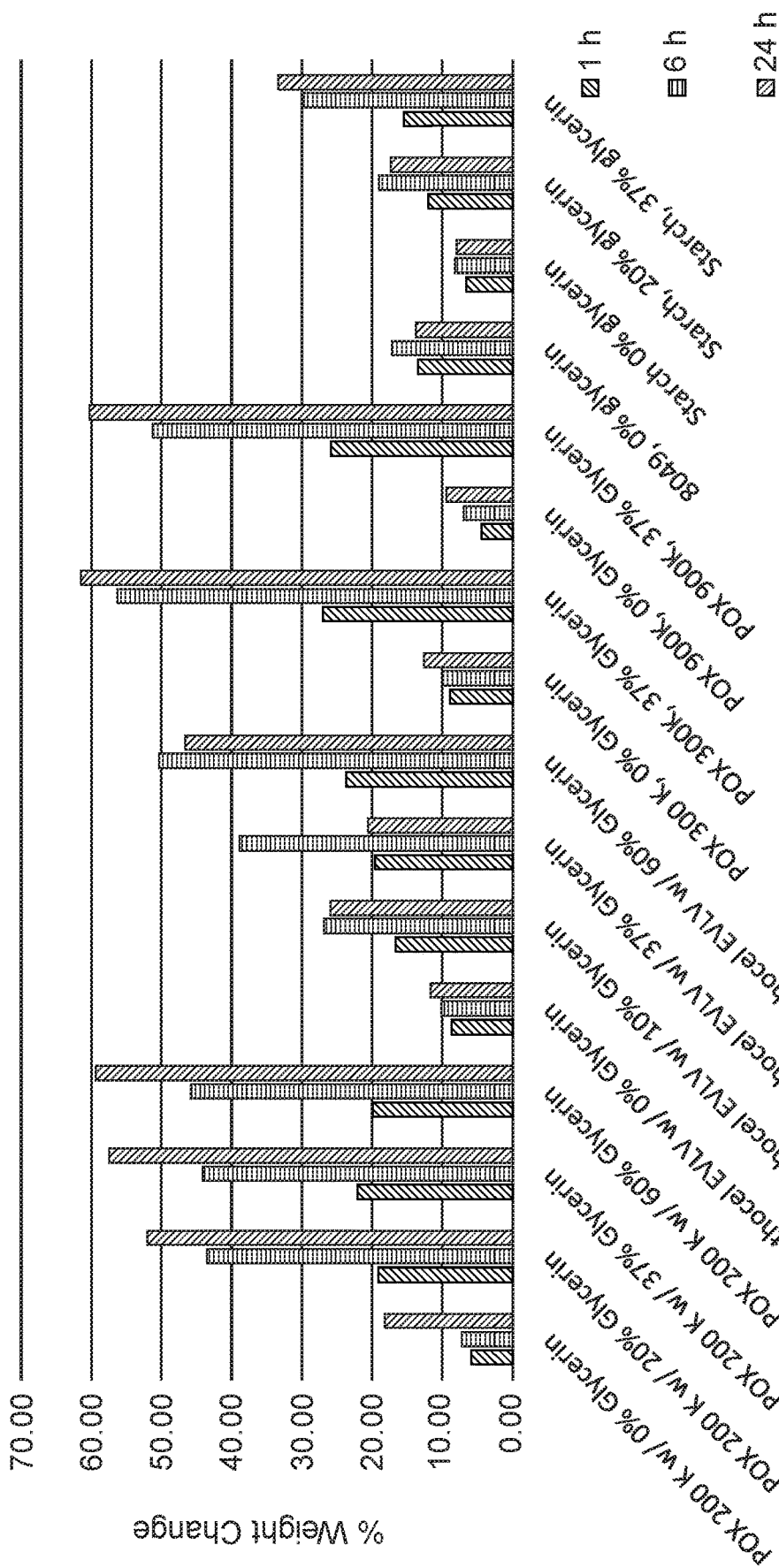
FIG. 7 is a bar graph that shows the effect of occlusion on the percentage of weight increase at 1 hour, 6 hours and 24 hours for certain water soluble film zones as described herein.

FIG. 7 is a bar chart that shows the effect of occlusion on the percentage of weight increase at 1 hour, 6 hours and 24 hours for certain water soluble film zones or water soluble films as described herein. Once the soluble film or product is exposed to a low water environment and/or is occluded on the skin as described herein, it has a weight change that is higher than the initial weight.

The water soluble film zone or product is also capable of decreasing in modulus as the buildup of water/humidity occurs under the product when applied to the skin. Thus the product or water soluble film zone provides a "dynamic" modulus where the modulus decreases during wear to improve the comfort of the product. In an aspect, the water soluble film, water soluble film zone, or product is capable of a reduction in modulus, of at least 90% or preferably at least about 95%, or from about 90% to about 100%, preferably from about 96% to about 100%, more preferably from about 97% to about 99% according to the Modulus test herein. As this transformation occurs, the skin active agent may be released from the product to the skin to have the intended effect.

Without being bound by theory, the soluble film zone or soluble film dissolves, disintegrates, and/or loses its physical integrity when exposed to low water environments. As the water soluble film zone or water soluble film softens and/or dissolves, the active is released. The soluble film zone or water soluble film, prior to exposure to a low water environment, is a dry film comprising a water soluble polymer. In this dry state it has a first modulus and the water soluble film zone, water soluble film or product also comprises a particular weight, e.g. an initial weight. In an aspect, once the soluble film or product is exposed to a low water environment and/or is applied to the skin so that the skin is occluded, as described herein, it has a second modulus that is lower than the first modulus and also has a second weight that is higher than the initial weight.

Table 1 shows the effect on the modulus of the product or water soluble film zone or water soluble film, when it is exposed to different temperature and humidity.

TABLE 1

| | Modulus (MPa) | | | | | | Modulus Drop [100* (Initial − Final)/Initial] | |
| --- | --- | --- | --- | --- | --- | --- | --- | --- |
| | 25 C. | | | 37 C. | | | 37 C. vs. 25 C. | |
| Sample No. | 40% RH | 75% RH | 90% RH | 40% RH | 75% RH | 90% RH | 75% vs. 40% | 90% vs. 40% |
| 1. Methocel E5LV 0% Glycerin | 1925 | 1122 | 61 | 1235 | 650 | 100 | 66.23 | 94.81 |
| 2. Methocel E5LV 37% Glycerin | 417 | 30 | 5 | 428 | 34 | 5 | 91.85 | 98.80 |
| 3. PEO 200K 0% Glyercin | 395 | 224 | 38 | 232 | 141 | 3 | 64.30 | 99.24 |
| 4. PEO 200K 37% Glycerin | 126 | 23 | | 116 | | | 100.00 | 100.00 |
| Foamed EVA Backing Layer | 22 | 23 | 24 | 14 | 14 | 14 | 36.36 | 36.36 |

Methocel E5LV is hydroxypropyl methylcellulose available from Dow Chemical.

In Table 1 25° C. represents the approximate temperature before the consumer puts the product on the skin, and 37° C. represents the approximate temperature when the consumer wears the product on the skin.

In one aspect the water soluble film zone has an initial modulus (at 25° C. and 40% RH) of about 30 MPa to about 600 MPa, preferably about 75 MPa to about 500 MPa, more preferably about 100 MPa to 450 MPa.

As is shown in Table 1, polyethylene oxide (PEO with a Mw of 200,000) with 37% glycerol has a % reduction in modulus of 100% at both 75% RH and 90% RH at 37° C. compared to the modulus at 25° C./40% RH. This same film material without glycerol in sample number 3 has a % reduction in modulus of 99.2% at 90% RH at 37° C. compared to the modulus at 25° C./40% RH.

Sample Number 2 with Methocel and 37% glycerol has a % reduction in modulus of 98.80% at 90% RH at 37° C. compared to the modulus at 25° C./40% RH.

As can be seen in Table 1, Foamed EVA, a material that may be used for the backing layer, shows a reduction in modulus of 36.36% at 90% RH at 37° C. compared to the modulus at 25° C./40% RH. In an aspect the backing layer comprises one or more layers of ethyl vinyl acetate, wherein the backing layer is capable of a modulus reduction of about 25% to about 50% when conditions change from 25° C./40% RH to 37° C./90% RH.

In an aspect, the water soluble film zone or water soluble film has a first modulus that is higher than the modulus of the backing layer or barrier patch. For example, after wearing on the skin at 37° C., at 90% RH, the water soluble film zone or water soluble film has a second modulus that is lower than the modulus of the backing layer or barrier patch. In an aspect this provides a product that is more comfortable to wear and more easily conforms around the curved surfaces of the skin, especially upon movement of the skin surfaces. Thus in an aspect, the ratio of modulus of soluble film to the modulus of backing layer or barrier patch is greater than 1 at 25° C./40% RH wherein the ratio is less than 1 at 37° C./90% RH. In another aspect the ratio of the modulus of the soluble film to the modulus of the backing layer or barrier patch is from about 0.2 to about 2 at 37° C./90% RH or from about 0.2 to about 1 at 37° C./90% RH.

In an aspect the ratio of the modulus of the water soluble film zone (or water soluble film) to the modulus of the EVA film backing layer changes from 5.7 (for PEO/37% glycerol) or 19 (methocel/37% glycerol) to <0.5 when changing conditions from 25° C./40% RH to 37° C./90% RH.

In an aspect the soluble film zone comprises a skin active agent. In an aspect the skin active agent is only minimally released, if at all, from the soluble film zone in the dry form prior to use and/or prior to exposure to the low water environment and/or in the absence of moisture or water. When a low level of water, contacts the soluble film zone, softening, dissolution or breakdown, begins to occur, thereby enabling the skin active to migrate out of the soluble film zone and/or penetrate to the skin surface or into the skin. In an aspect in the presence of water, skin active agents present in the soluble film zones are believed to be more readily available to the skin due to the faster rates of diffusion through the soluble film zone.

In an aspect, prior to use by the consumer, the water soluble film zone is substantially free of water or may comprise less than about 15%, 12%, or 10%, water, or comprise about 0.001% to about about 15% water, or about 0.05% to about 10%, water, by weight of the soluble film zone.

Preferred water-soluble materials for the soluble film zone are polymeric materials, preferably polymers which may be formed into a film or sheet. The water-soluble film zone can, for example, be obtained by casting, blow-molding, extrusion or blown extrusion of the polymeric material, as known in the art.

Preferred water-soluble materials for the soluble film zone may be selected from polyethylene oxide polymers, polyvinyl alcohols, polyvinyl pyrrolidone, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum, polyacrylates and water-soluble acrylate copolymers, polymethacrylates, methylcellulose, carboxymethylcellulose, hydroxyethyl cellulose, hydroxypropyl methylcellulose, dextrin, maltodextrin, salts thereof, and combinations thereof.

Additional water-soluble materials for the soluble film zone may be selected from polyethylene glycol, pullulan, carbohydrate polymers such as natural polysaccharide or derivates including pectin and derivatives, sodium alginate, methyl methacrylate copolymer, carboxyvinyl polymer, amylase, pectin, chitin, chitosan, levan, elsinan, collagen, gelatine, zein, gluten, soy protein isolate, whey protein isolate, casein, gums (such as guar, gum Arabic, tragacanth gum, xanthan gum, gellan sodium salt, gum ghatti, okra gum, karaya gum, locust bean gum, tara gum, quince seed gum, fenugreek seed gum, scleroglucan, psyllium seed gum, tamarind gum, oat gum, quince seed gum, rhizobium gum, biosynthetic gums, Khaya grandifolia gum, pectin, arabian, Konjac mannan, alactomannan, funoran, acetan, welan, rhamsan, furcelleran, succinoglycan, scleroglycan, and dextran, flaxseed gum), propyleneglycol, alginate, starches (such as amylose, amylopectin, modified starches, hydroxyethyl starch, carboxymethyl starch, high amylose starch, hydrooxypropylated high amylose starch, biosynthetic processed starch, starches such as rice, corn, potato, and wheat), dextrans, dextrins and maltodextrins, konjac, acemannan from aloe, carrageenans, scleraglucan, succinoglucan, larch arabinogalactan, chondroitin sulfates, hyaluronic acid, curdlan, deacetylatedkonjac, water soluble non-gelling polypeptide or protein (such as gelatins, albumins, milk proteins, soy protein, and whey proteins), hydrocolloids (such as synthetic hydrocolloids exemplified by polyethylene-imine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrollidone, polyethylene glycols, polyethylene oxides, polyvinyl alcohols, pluronics, tetronics, and other block co-polymers, carboxyvinyl polymers, and colloidal silicon dioxide, soluble polyesters, natural seaweeds, natural seed, natural plant exudates, natural fruit extracts, glycyrrhizic acid, polyacrylic acid, vinyl polymers, cationic polymers, acrylic polymers (such as sodium polyacrylate, polyethyleacrylate and polyacrylamide), and combinations.

In an aspect the water soluble film zone comprises a polymer selected from the group consisting of polyethylene oxide polymer, polyvinyl alcohols, polyvinyl alcohol copolymers, starch, methylcellulose, carboxymethylcellulose sodium, hydroxyethyl cellulose, hydroxypropyl methylcellulose and combinations.

Preferred polymers, copolymers or derivatives thereof suitable for use as water-soluble film for the soluble film zone are selected from polyethylene oxides, and combinations thereof.

Preferred polymers, copolymers or derivatives thereof suitable for use as water-soluble film for the soluble film zone are selected from methylcelluloses, and combinations thereof.

Preferred water-soluble film forming polymers are made from polyethylene oxides such as polyethylene oxide films or polyethylene glycol, and include Polyox, sold by the Dow Chemical Company. Polyethylene oxides include Polyox WSR N-10 (having a molecular weight of 10,000), WSR N-80 (with a molecular weight of about 200,000), WSR N750 (with a molecular weight of about 300,000) of corresponding solubility characteristics. In an aspect the water soluble film comprises a polyethylene oxide having a molecular weight from about 500 to about 10,000,000 or from about 10,000 to about 1,000,000 or from about 100,000 to about 300,000 or from about 150,000 to about 250,000.

Another preferred water soluble film forming polymer is Methocel E5LV, a water soluble cellulose ether of low viscosity available from Dow/Coloron LTD.

The polyethylene oxide polymers or cellulose ether may be combined with additional polymers, for example, polymers, copolymers or derivatives thereof which may be other water-soluble film forming polymers. The additional polymers may be selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum, polyacrylates and water-soluble acrylate copolymers, polymethacrylates, methylcellulose, carboxymethylcellulose, hydroxyethyl cellulose, hydroxypropyl methylcellulose, dextrin, maltodextrin, salts thereof, and combinations thereof. In an aspect the water soluble film zone comprises polyethylene oxide polymer and an additional polymer selected from the group consisting of polyvinyl alcohols, polyvinyl alcohol copolymers, starch, methylcellulose, carboxymethylcellulose sodium, hydroxyethyl cellulose, hydroxypropyl methylcellulose and combinations.

Also suitable are mixtures of polyethylene oxide polymers having different molecular weights. The additional polymers may have molecular weights, preferably from about 1,000 to 1,000,000, more preferably from about 50,000 to 300,000 yet more preferably from about 20,000 to 150,000.

Preferably, the level of polymer in the water-soluble film zone in the dry state, is from about 20% to about 90%, or from about 45% to about 85% or from about 50% to about 70% by weight of the water soluble polymer zone.

In another aspect, the cosmetic composition may comprise a water in oil or an oil in water emulsion to be combined with a water soluble film forming polymer. As an example, an oil in water emulsion composition such as Olay skin care product may be combined with methylcellulose or hydroxypropyl methylcellulose such as Methocel E5LV (available from Dow Chemical) and used as the water soluble film zone. The water soluble film forming polymer, such as Methocel, may be used in excess of the composition comprising the oil in water emulsion and skin active agent. In an aspect, thus, the water soluble film zone may comprise:
  a.) from about 40% to about 70% by weight of the soluble film zone, of a water soluble film forming polymer;
  b.) from about 30% to about 60% by weight of the soluble film zone, of a cosmetic composition comprising a water in oil or an oil in water emulsion and an effective amount of a skin active agent and optionally a safe and effective amount of a plasticizer.

In an aspect, the ratio of b) to a) in the soluble film zone, is from about 30:70 to about 70:30 or from about 40:60 to about 60:40 or about 45:55 to about 55:45 in either the wet or dry state.

Plasticizer

The water soluble film zone herein can also comprise one or more plasticizers. For example, it can be beneficial to add plasticizers at a level of from about 2% to about 80% or about 2% to about 60%, by weight of the soluble film zone or the water soluble film forming polymer, or from about 0.10% to about 50% or from about 20% to about 45% by weight. The plasticizers may be, for example, glycerol, ethylene glycol, diethylene glycol, hexylene glycol, triethylene glycol, propylene glycol, polyethylene glycol, polypropyl glycol, alkyl citrate, sorbitol, pentaerythritol, glucamine, N-methylglucamine, sodiumcumenesulfonate and mixtures thereof. In one aspect the plasticizer is glycerol. Other plasticizers may include vegetable oil, polysorbitols, polyethylene oxide, dimethicone, mineral oil, paraffin, C1-C3 alcohols, dimethyl sulfoxide, N, N-dimethylacetamide, sucrose, corn syrup, fructose, dioctyl-sodium-sulfosuccinate, triethyl citrate, tributyl citrate, 1,2-propyleneglycol, mono, di- or triacetates of glycerol, natural gums, citrates, and mixtures thereof.

Optional Ingredients for Soluble Film Zone

The water soluble film zone or water soluble film forming polymer herein can also comprise one or more optional ingredients. Optional ingredients include bulking agents, fillers, diluents, surfactants, stabilizing agents, emulsifiers, thickeners, preservatives, binders, colorants, pigments, solubilizing agents, wetting agents, water soluble inert fillers, buffering agents, permeation enhancers, and combinations. Thickeners may include gum arabic, carrageenan, karaya gum, gum tragacanth, carob gum, quince seed or Cydonia oblonga, casein, dextrin, gelatin, sodium pectate, sodium alginate, methyl cellulose, ethyl cellulose, CMC, hydroxy ethyl cellulose, hydroxypropyl cellulose, polyvinyl alcohol, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate or beagum, laponite, and silicic acid anhydride.

Surfactants may include mono and diglycerides of fatty acids and polyoxyethylene sorbitol esters, such as, Atmos 300 and Polysorbate 80, pluronic acid, and sodium lauryl sulfate.

Stabilizing agents may include xanthan gum, locust bean gum and carrageenan, guar gum, sugars, polyols, amino acids or methylamines. Emulsifying agents may include triethanolamine stearate, quaternary ammonium compounds, acacia, gelatin, lecithin, bentonite, veegum, sodium benzoate.

Permeation enhancers may include azone, alcohol, dimethyl-sulfoxide, monovalent, saturated and unsaturated aliphatic and cycloaliphatic alcohols having 6 to 12 carbon atoms such as cyclohexanol, lauryl alcohol, and the like; aliphatic and cycloaliphatic hydrocarbons such as mineral oil; cycloaliphatic and aromatic aldehydes and ketones such as cyclohexanone; N,N-di(lower alkyl)acetamides such as N,N-diethyl acetamide and N,N dimethyl acetamide, N,N-dimethyl acetamide, N-(2-hydroxyethyl)acetamide and the like; aliphatic and cycloaliphatic esters such as isopropyl myristate and lauricidin; N,N-di(lower alkyl) sulfoxides such as decylmethyl sulfoxide; essential oils, nitrated aliphatics, aliphatic and cycloaliphatic hydrocarbons such as N-methyl-2-pyrrolidone and azone; salicylates, polyalkylene glycol silicates; aliphatic acids such as oleic acid and lauric acid, terpines such as cineole, siloxanes such as hexamethyl siloxane; and mixtures.

Discussion of the Figures

Figure 2A:
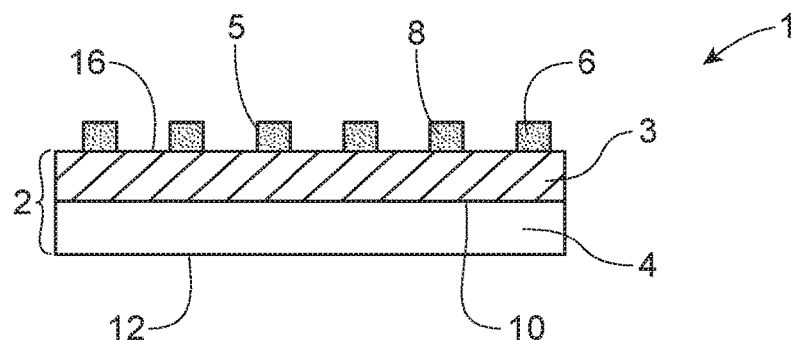
FIG. 2A is a cross section taken along 2A-2A of FIG. 1.

Exemplary aspects of the product 1 are shown in FIGS. 1, 2A, 2B, 3 and 4. FIGS. 1, 2 A and 2B show product 1 comprising a barrier patch 2 having a pressure sensitive adhesive 3 and a backing layer 4. FIG. 2A is the cross section of FIG. 1 taken along 2A-2A. FIG. 1 shows a plurality of soluble film zones 6 to create a series of parallel stripes offset to the longitudinal axis of the product 1. The product 1 thus has alternative rows of stripes of the soluble film zones 6 applied to the upper surface 16 of the pressure sensitive adhesive 3.

The product 1 further comprises a soluble film zone 6 having an effective amount of a skin active agent 8. The backing layer 4 further comprises a first surface 10 and a second surface 12. The pressure sensitive adhesive 3 is in contact with at least part of the first surface 10 of the backing layer 4 to form a pressure sensitive adhesive coated region 14 of the first surface 10. The product 1 may further comprise a cosmetic composition comprising an effective amount of a skin active agent 8. In one aspect the pressure sensitive adhesive 3 also comprises the cosmetic composition. In other aspects the cosmetic composition and skin active agent 8 is distributed to some extent and/or is homogeneously distributed throughout the soluble film zone 6. The product 1 has a skin facing surface 5. The skin facing surface 5 of the product 1 may comprise the upper surface 16 of the pressure sensitive adhesive, the top surface 22 of the water soluble film zone and/or the first surface 10 of the backing layer.

In the aspect of FIGS. 1, 2A, 2B, and 3, the products 1 and 40 are crescent shaped. However this shape is not intended to limit the invention.

Figure 2B:
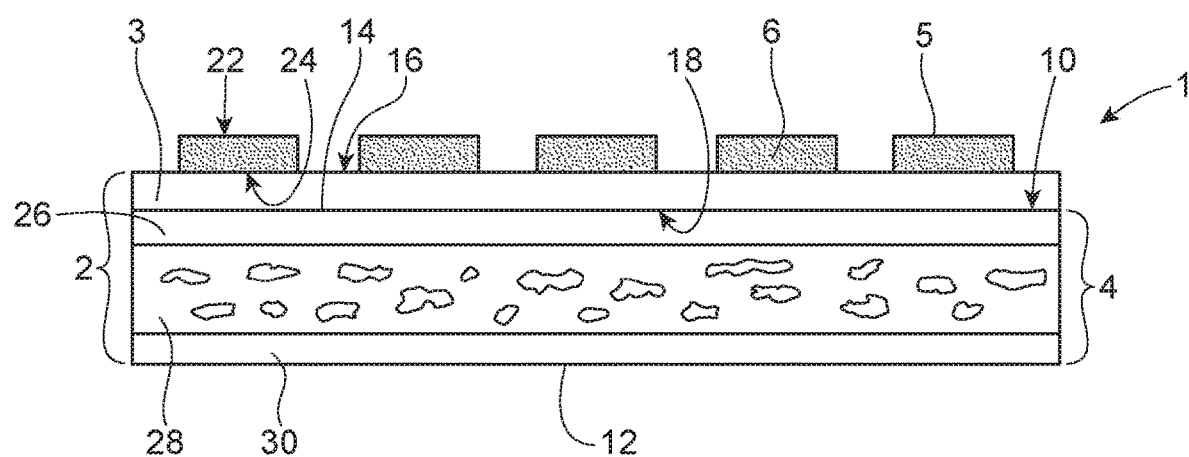
FIG. 2B is an alternative cross section of a beauty care product as shown and described herein.

FIG. 2B is an alternative cross section of the product of FIG. 1 also taken along 2A-2A. FIG. 2 B shows the product 1 comprising a barrier patch 2 having a pressure sensitive adhesive 3 and a backing layer 4. The product 1 further comprises a soluble film zone 6 having an effective amount of a skin active agent 8. The backing layer 4 further comprises a first surface 10 and a second surface 12. The pressure sensitive adhesive 3 is in contact with at least part of the first surface 10 of the backing layer 4 to form a pressure sensitive adhesive coated region 14 of the first surface 10. The backing layer 4 comprises 3 layers: a non-foamed first layer 26, a foamed second layer 28 and a non-foamed third layer 30. The pressure sensitive adhesive comprises an upper surface 16 and a lower surface 18. The soluble film zone 6 also comprises a top surface 22 and a bottom surface 24. As shown in FIG. 2B the bottom surface 24 of the plurality of soluble film zones 6 are in contact with the upper surface 16 of the pressure sensitive adhesive 3. As shown in FIGS. 1, 2A and 2B the soluble film zones 6 and the pressure sensitive adhesive 3 are substantially separate and the pressure sensitive adhesive zone 6 is continuous.

Figure 3:
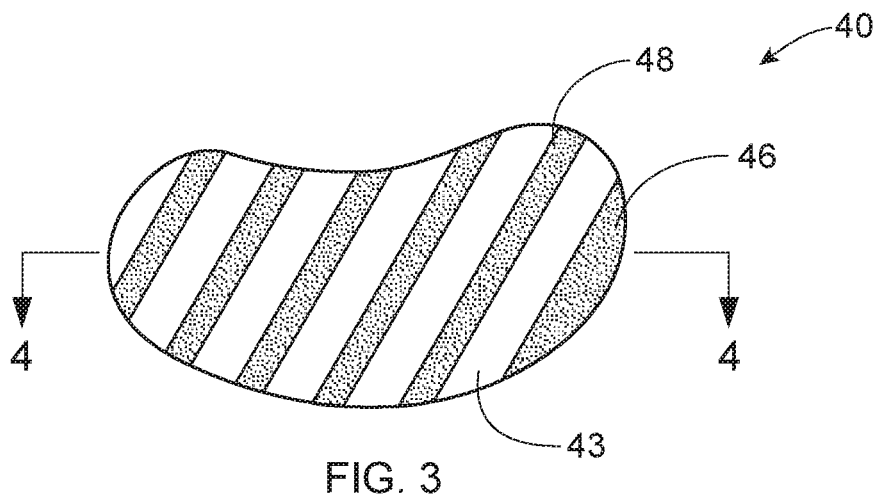
FIG. 3 is a top plan view of a beauty care product comprising discontinuous water soluble film zones and discontinuous pressure sensitive adhesive zones, as shown and described herein.
Figure 4:
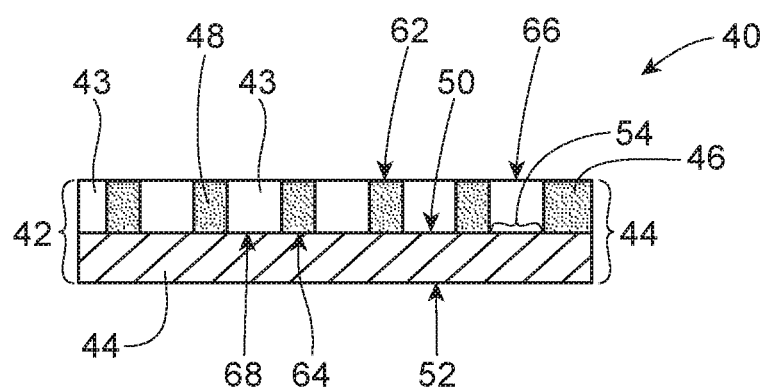
FIG. 4 is a cross section taken along 4-4 of FIG. 3.

FIGS. 3 and 4 show a product 40 comprising a barrier patch 42 having a pressure sensitive adhesive 43 and a backing layer 44. FIG. 4 is the cross section of FIG. 3 taken along 4-4. The product further comprises a plurality of discontinuous soluble film zones 46 having an effective amount of a skin active agent 48. The backing layer 44 further comprises a first surface 50 and a second surface 52. The pressure sensitive adhesive 43 is in contact with at least part of the first surface 50 of the backing layer 44 to form a plurality of pressure sensitive adhesive coated regions 54 of the first surface 50 of the backing layer 44. The product 40 may further comprise a cosmetic composition comprising an effective amount of a skin active agent 48. In one aspect the skin active agent 48 is distributed to some extent and/or homogeneously distributed throughout each of the plurality of the soluble film zones 46. As shown in FIGS. 3 and 4, the plurality of soluble film zones 46 and the adhesive zone 43 are substantially separate. In FIG. 4 the soluble film zones 46 are in contact with the first surface 50 of the backing layer 44. As shown in FIG. 4, in an aspect the top surface 62 of the soluble film zones and the upper surface 66 of the pressure sensitive adhesive zone 43 are co-planar or collinear. In addition the bottom surface 64 of the soluble film zone and the lower surface 68 of the pressure sensitive adhesive zone may be co-planar or collinear.

Figure 5:
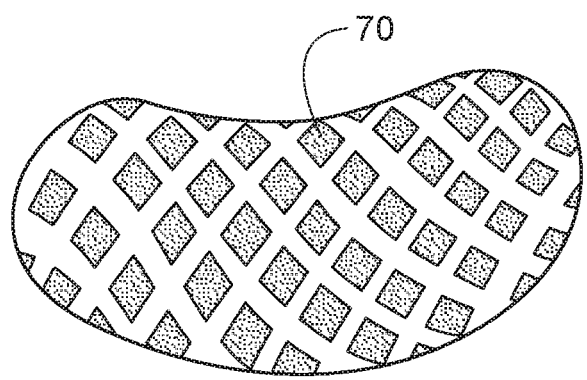
FIG. 5 shows a product showing an alternative pattern of discontinuous water soluble film zones.

FIG. 5 shows a product showing an alternative pattern of discontinuous soluble film zones 70, wherein the soluble film zones 70 are configured as a series of repeating diamonds.

Figure 6:
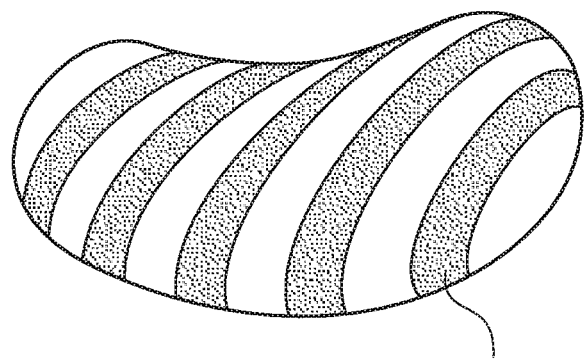
FIG. 6 shows a product showing an alternative pattern of the discontinuous water soluble film zones.

FIG. 6 shows a product showing an alternative pattern of the discontinuous soluble film zones 72 wherein the soluble film zones 72 are a series of repeating curved stripes.

FIG. 7 is a bar chart that shows the effect of occlusion on the percentage of weight increase at 1 hour, 6 hours and 24 hours for certain water soluble film zones as described herein.

Figure 8:
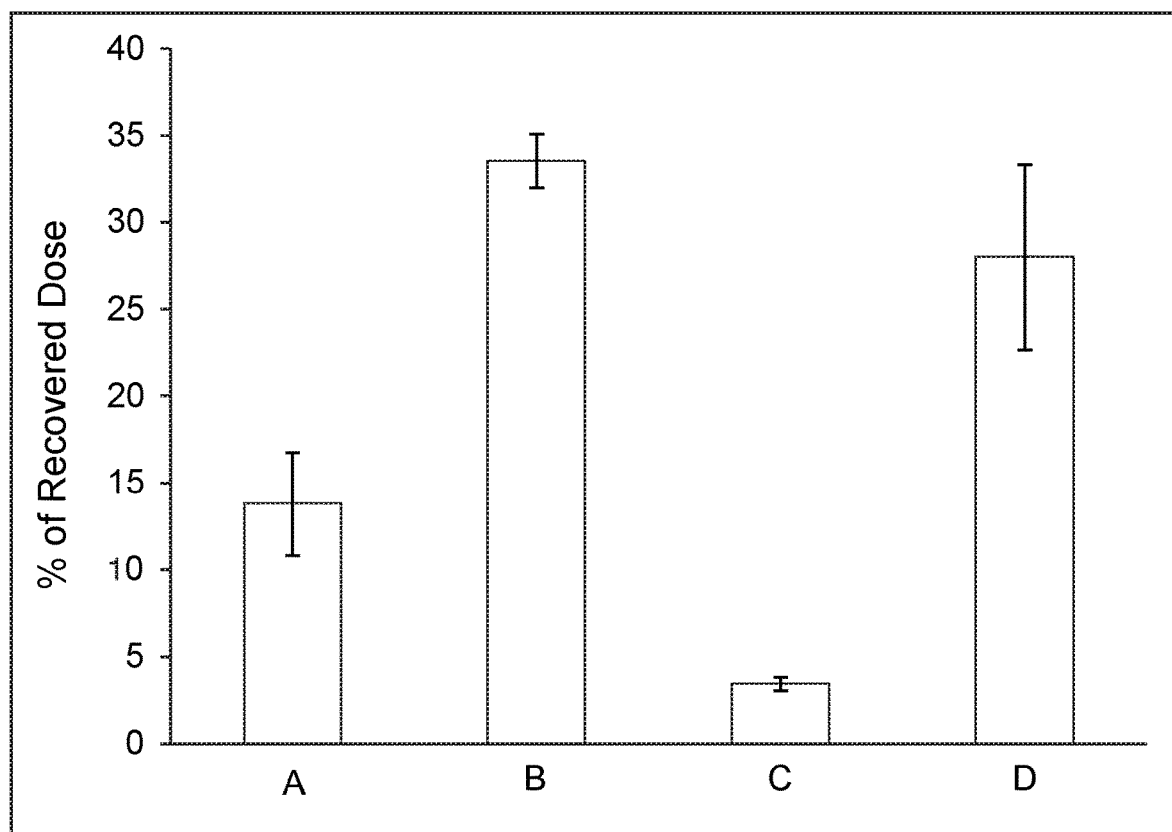
FIG. 8 shows a bar graph representing Franz cell penetration of actives.

FIG. 8 represents Franz cell penetration for data for (A) in an oil in water emulsion applied without occlusion; (B) an oil in water emulsion occluded by polyethylene terephthalate (PET) film; (C) Methocel E5LV film applied without occlusion; and (D) Methocel E5LV film occluded by PET film. Both the emulsions and the Methocel films each contained 2% inositol. These data demonstrate that the Methocel E5LV in the form of a dry film, without occlusion via a backing layer, does not or only minimally releases inositol, but when it is occluded, the Methocel. E5LV film dissolves and the inositol is released. The same is true for the emulsion. Thus the backing layers herein that provide occlusion via e.g. low WVTR, increase delivery of the active to the skin. Franz cell apparatus may be used for the in-vitro assessment of penetration of actives such as inositol through a skin mimic after the application of the sample following pre-treatment with a protective composition. Penetrated actives such as inositol may be quantified using Reverse Phase High Performance (or Pressure) Liquid Chromatography (RP-HPLC) with external standard quantitation at 240 nm. See, for example, the Franz cell procedure in P&G's EP2561.856 A1.

Barrier Patch

In an aspect the barrier patch may comprise a backing layer having a first surface and a second surface and a WVTR from about 1 g/m$^2$/24 h to about 500 g/m$^2$/24 h; and a pressure sensitive adhesive zone, having a upper surface and a lower surface, and the pressure sensitive adhesive may be in contact with the first surface of the backing layer.

The backing layer may be a co-extruded film laminate comprising at least two layers, but can comprise 3, 4, 5, 6, or more layers. In an aspect the backing layer or product or non-foamed first layer is substantially free of apertures.

"Apertures" as used herein means films having openings of a size and shape that allow for liquid molecules to pass through the film.

The barrier patch of the present invention may comprise a solid sheet material. The sheet provides the primary structure and shape to the product, allowing it to be handled and applied for treatment of a specific target area of the skin.

In certain aspects, backing layer is generally made of a flexible film material which is capable of remaining fitted and flexing during the movement of the human body and movements especially associated with facial expressions or gestures. By "flexible" it is meant that the product, barrier patch, and/or the backing layer may be substantially bent or folded without breaking, tearing, ripping, etc.

In an aspect the product or barrier patch also does not collapse or fold under gravity or upon handling and application by the user. It is desirable for the product to conform to the target area of the skin surface to which it is applied without folding, crinkling, or inducing more wrinkling of the target area of the skin. Accordingly, the product or barrier patch is readily conformable to the skin and remains flexible throughout the duration of use, as the user moves during the period of time worn.

In certain aspects a feature of the subject product is that the barrier patch, adhesive zone, and/or the backing layer are substantially free of, comprises only non-effective amounts of, or is free of or void of, a skin active agent. As such, the barrier patch, the adhesive zone, and/or the backing layer of the present invention may be characterized as a "blank" backing layer, adhesive zone, or barrier patch. In this regard, in an aspect, an effective amount of the skin active agent employed in the product herein is substantially separate from the barrier patch, the adhesive zone, and/or the backing layer. In an aspect the pressure sensitive adhesive zone and water soluble film zone are substantially separate. The term "substantially separate" as used herein means that one component is substantially free of the other component.

In one aspect the backing layer may be a laminate comprising a film and a non-woven material for example, cotton, rayon, acrylic fibers, polypropylene fibers, polyester fibers and combinations, provided that the laminate comprises a WVTR from about 1 g/m$^2$/24 h to about 500 g/m$^2$/24 h.

The one or more layers of the barrier patch may comprise at least one material that includes but is not limited to polypropylene (PP); polyethylene (PE), metallocene plastomers, metallocene elastomers, high density polyethylene (HDPE), rubber modified LDPE, rubber modified LLDPE, acid copolymers, polysytyrene, cyclic polyolefins, polyethylene terephthalate (PET); polyvinylchloride (PVC); polyamide (PA); polycarbonate; polyurethane; cellulose acetate; polychloropene; polysulfone; polytetrafluoroethylene (PTFE); polyvinyl acetate (PVA); polyethylene glycol terephthalate film; polystyrene; polyphenylene oxide (PPO); acrylonitrile butadiene styrene (ABS); acrylic; acrylonitrile styrene acrylate (ASA); ethylene vinyl alcohol, natural rubber, latex, nylon, nitrile, silicone and thermo plastic elastomers (TPE), ethylene vinyl acetate (EVA), ethylene acrylic acid (EAA), copolymers of PE with PP, bimodal resins, any of which may be from either homopolymers or copolymers, and blends and combinations of these materials. Blends may be physical blends or reactor blends. The layers may comprise a single polymer or mixtures of polymers or copolymers. Laminates of these layer materials may also be used.

The backing layer(s) herein may comprise polyethylene. The term "polyethylene" or "PE" is used herein the broadest sense to include PE of any of a variety of resin grades, density, branching length, copolymer, blend, catalyst, and the like. The layer may comprise a blend of different grades of polyethylene, that may include LLDPE, LDPE, VLDPE, HDPE, or MDPE, or combinations thereof; manufactured using Ziegler-Natta catalysts, Chromium catalysts, metallocene based catalysts, single site catalysts, and other types of catalysts. The polymers may be homopolymers or copolymers. Blends may be physical blends or reactor blends. These materials can be bio-based, petro-based and recycled/reground. LLDPE copolymers can be made with any one or more of butene, hexene and octene comonomers. The ratio of the different grades can vary.

A preferred material for the one or more layers of the backing layer includes ethylene vinyl acetate, EVA (CAS No. 24937-78-8) copolymer. Different grades of EVAs tend to have different ethylene-to-vinyl acetate monomer ratios and/or different melt indices (molecular weights). For example the percentage of VA monomer may range from about 20% to about 50% or from about 25% to about 40% of VA or from about 25% to about 30% of VA. For example the melt flow index may range from about 0.7 dg/min to about 60 dg/min and/or from about 2 dg/min to about 6 dg/min and/or from about 2 dg/min to about 4 dg/min. EVA grades useful herein include Dupont Elvax® Grades: 260 (28% VA; Melt Flow Index MFI 6 dg/min via ASTM D1238); Grade 250 (28% VA; MFI 25 dg/min); Grade 150 and 150W (32% VA; MFI 43 dg/min); Grade 40 W (40% VA; MFI 52 dg/min); and Celanese Ateva® 2803G (28% VA; MFI 3 dg/min via ASTM D1238) and Ateva® 1807EG (18% VA; MFI 0.7 dg/min).

Another preferred material for the backing layer or barrier patch is a polyethylene film sold under the tradename, 1525L, available from 3M, St. Paul, Minn. 3M 1525-L has a backing of polyethylene film of approximately 3 mil thickness, a 1.4 mil thick hypoallergenic, pressure sensitive acrylate adhesive layer and a paper release layer coated with polyethylene and silicone (3M 1525L may be used without the release layer).

A color masterbatch containing pigment and/or slip/anti-block agent and/or liquid colorants can also be added to the backing layer to afford certain aesthetics and functionality.

Pigments if present may typically be used in concentrations of about 0.5 wt. % to about 15 wt. %, and/or from about 1 wt. % to about 10 wt. %, or from 1.5 wt. % to about 7 wt. %, based on the total weight of the polymer (e.g. of the backing layer).

Other additives are further detailed in U.S. patent publications including U.S. patent application Ser. No. 13/924,983, filed Jun. 24, 2013 (P&G US 2014/0376835; Case 12966Q); and U.S. patent application Ser. No. 13/924,999, filed Jun. 24, 2013 (P&G Case 12967Q), and the references cited therein.

For example the backing layer of the barrier patch optionally can include an additive such as a slip agent or an antistatic agent (e.g., euracamide, a steramide), a filler (e.g., talc, clay, pulp, titanium dioxide, thermoplastic starch, raw starch wood flour, diatomaceous earth, silica, inorganic glass, inorganic salts, pulverized plasticizer, pulverized rubber), a pigment (e.g., mica, titania, carbon black), a UV inhibitor, an anti-coloring agent, a mold release agent, a flame retardant, an electrically conductive agent, an antioxidant, an impact modifier, a stabilizer (e.g., a UV absorber), wetting agents, carbon, graphene and a biodegradable-enhancing additive (e.g., an oxo-degradable additive or an organic material). An oxo-degradable additive is often compounded into a polymer in a concentration of about 1 wt. % to about 5 wt. %, based on the total weight of the polymer, and includes at least one transition metal that can foster oxidation and chain scission in plastics when exposed to heat, air, light, or mixtures thereof. Organic materials (e.g., cellulose, starch, ethylene vinyl acetate, and polyvinyl alcohol) also can be used as biodegradable-enhancing additives, although they cannot promote degradation of the non-degradable portion of the polymer matrix.

In a preferred aspect, the multi-layered co-extruded backing layer has at least three layers, and is preferably a ethylene vinyl acetate ("EVA") comprising film. In a preferred aspect, a foamed layer is in-between layers of non-foamed layers, e.g. the non-foamed first layer and the non-foamed third layer, on either side.

In one aspect the barrier patch comprises a backing layer comprising:
 (i) a non-foamed first layer comprising a non-foamed polymer film having a first surface;
 (ii) a foamed second layer comprising a foamed polymer film comprising a Mean Void Volume Percentage from 45% to 80%, preferably from 50% to 75%, more preferably from 55% to 73%, and a thickness of from 10 microns to 250 microns, preferably from 40 microns to 160 microns.

The technique for measuring Mean Void Volume Percentage is described in U.S. Ser. Nos. 62/257,341; 62/257,347 and 62/257,351. The degree of foaming of a foamed layer may be characterized by a Mean Void Volume Percentage, as determined by X-ray micro-computed tomography or simply "microCT."

In one aspect, the foamed layer comprises from 45% to 80% of a Mean Void Volume Percentage (relative to the volume of the foamed layer in total), preferably from 50% to 75%, more preferably from 55% to 73%, Mean Void Volume Percentage.

In an aspect the backing layer of the barrier patch comprises three layers, e.g. a foamed second layer optionally comprising EVA and a layer of non-foamed EVA on either side, i.e., a first non-foamed EVA layer and a third non-foamed EVA layer wherein the foamed EVA layer is in-between said first and third non-foamed layers.

In one aspect the multi-layer barrier patch and/or the backing layer is substantially free of fiber, nanofibers, or non-woven material for example, cotton, rayon, acrylic fibers, polypropylene fibers, polyester fibers.

In another aspect the barrier patch and/or backing layer includes a corona treatment. For example, the backing layer or barrier patch may be additionally treated, for example by corona discharge or coating with an adhesion promoter which as a primer may effect anchoring of the active and adhesive.

The material composition and/or polymer resins used in the foamed layer may be different from those used in the non-foamed layer(s), since the material composition and/or resins may be optimized for foam formation, or other film layer properties. Additives, particularly small amount of nucleating agents selected from the group consisting of $CaCO_3$, clays, talcs, and combinations thereof, may be included for quick bubble formation during foaming process.

The resin used in making the backing layer(s) of the barrier patch may include renewable materials, either "bio-identical" or "bio-new" materials, or a combination thereof. Some non-limiting options of applicable bio-identical and/or bio-new materials are further detailed in U.S. patent publications from U.S. patent application Ser. No. 13/924,983, filed Jun. 24, 2013 (P&G US 2014/0376835), at pages 15-22; and U.S. patent application Ser. No. 13/924,999, filed Jun. 24, 2013 (P&G US 2014-0377512 A1; P&G Case 12967Q) at pages 12-20. For example the barrier patch may include at least one layer made of a plastic resin. The resin could be a traditional petro-based polyolefin, or it could be a renewable based polyolefin, or a blend thereof. Alternatively it could be a blend comprising a petro-based or renewable based polyolefin blend mixed with a renewable "bio-new" material that is chemically different to traditional petro-based polyolefins. The film layer could be comprised of a material or mixture of materials having a total bio-based content of about 10% to about 100% using ASTM D6866-10, method B. In one aspect, the layer may comprise from about 5% to about 99% by weight of a polymer (A) comprising at least one or possibly more of a low density polyethylene (LDPE), a polar copolymer of polyethylene such as ethylene vinyl acetate (EVA), a linear low density polyethylene (LLDPE), a high density polyethylene homopolymer/high density polyethylene copolymer, a medium density polyethylene, a very low density polyethylene (VLDPE), a plastomer, a polypropylene/copolypropylene/heterophasic polypropylene, polyethylene terephthalate (PET), PLA (e.g., from Natureworks), polyhydroxyalkanoate (PHA), poly(ethylene-2,5-furandicarboxylate) (PEF), cellulose (available from, for example, Innovia), NYLON 11 (i.e., Rilsan® from Arkema), starch (either thermoplastic starch or starch fillers), bio-polyesters, (e.g., those made from bioglycerol, organic acid, and anhydride, as described in U.S. Patent Application No. 2008/0200591, incorporated herein by reference), polybutylene succinate, polyglycolic acid (PGA), and polyvinyl chloride (PVC). At least one of the constituents of polymer (A) may be at least partially derived from a renewable resource. Recycled materials may also be in added. In specific cases, materials that are biodegradable may be utilized.

Some of the "bio-new" materials may further contribute to reflectivity of the film, as the presence of this additional material within the film layer structure can lead to additional light reflectivity, due to their typical incompatibility with the polyolefin matrix.

Adhesive Zone

The barrier patch may comprise a backing layer and pressure sensitive adhesive zone. Typically, the pressure sensitive adhesive zone comprises a pressure-sensitive adhesive (PSA) that is suitable for long-term skin contact, and which should be physically and chemically compatible with the backing layer and/or additives that are present. Examples of suitable adhesive materials include, but are not limited to, the following: acrylic and methacrylic ester homo- or copolymers, butyl rubber based systems, silicones, urethanes, vinyl esters and amides, olefin copolymer materials, natural or synthetic rubbers, hot-melt adhesives (see, for example, U.S. Pat. No. 5,387,450); polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene) and combinations thereof.

According to one aspect the adhesive is a hotmelt adhesive including adhesives selected from the group consisting of ethyl vinyl acetate, metallocene polyalphaolefins, polyolefins including atactic polyalphaolefins, block copolymers such as diblocks copolymers and triblock copolymers, polyurethane hot melts, polyamides and combinations thereof. In one aspect the adhesive comprises a combination of diblock copolymers and triblock copolymers. Diblocks and triblock copolymers may include styrene/isoprene; styrene/butadiene; butylene/ethylene/styrene; and combinations thereof.

High viscosity triblock copolymers may be used as adhesives and have the configuration A-B-A wherein the polymer blocks A are non-elastomeric polymer blocks which, as homopolymers have glass transition temperatures above 20° C. The elastomeric polymer blocks, B, are generally isoprene or butadiene which may be partially or substantially hydrogenated or mixtures thereof. Further, the copolymers may be linear or branched.

Diblock copolymers may generally have the A-B configuration where A and B are as described previously.

Liquid diluents may be added to the adhesive compositions. The adhesive composition may comprise from about 60% to about 99% diluents, by weight. In an aspect the majority of the liquid diluent is oil. Preferably the liquid diluent comprises, or consists essentially of, oils such as highly refined white petroleum mineral oil. Useful diluents are primarily aliphatic in character and compatible with the polymer midblock. Plasticizers may also be included, e.g. paraffinic and naphthenic petroleum oils, highly refined aromatic-free paraffinic and naphthenic food and technical grade oils, highly refined white petroleum mineral oils, and liquid tackifiers such as the synthetic liquid oligomers of polybutene, polypropene, polyterpene, etc. The synthetic process oils may be high viscosity oligomers which may be permanently fluid/liquid monoolefins, isoparaffins or paraffins of moderate to high molecular weight.

In an aspect the adhesive is selected from the TECHNOMELT® and DERMA-TAK® brands available from Henkel, for example TECHNOMELT PSM 154A DERMA-TAK®. DERMA-TAK products are pressure-sensitive adhesives and encompass both solvent-based acrylic and formulated rubber (liquid and hotmelt) pressure-sensitive adhesives. Useful adhesives may also be selected from those described in U.S. Pat. Nos. 6,448,303 and 5,559,165.

In an aspect the pressure sensitive adhesive zones are continuous, discontinuous, or a combination thereof. The product may also comprise a plurality of discontinuous adhesive zones.

Thickness

In one aspect, the overall total thickness of the barrier patch or the product is from 20 microns to 500 microns, preferably from 50 microns to 200 microns, more preferably from 70 to 180 microns, yet more preferably from 75 to 150 microns and combinations thereof.

In another aspect the water soluble film zone (dry state) has a total thickness of about 2 microns to about 200 microns, preferably from 50 microns to about 175 microns, more preferably from about 75 to about 170 microns. In an aspect, the water soluble film zone in the dry state, has a thickness of about 5 microns to about 50 microns, or about 15 microns to about 30 microns.

In an aspect the pressure sensitive adhesive zones typically have an average thickness ranging from about 5 microns to about 350 microns, in alternative aspects about 10 microns to about 120 microns.

In an aspect the typical basis weight for the product herein ranges from about. 40 to about 190 gsm, for instance about 45 gsm to about 170 gsm and/or from about 50 gsm to about 140 gsm.

Continuous or Discontinuous Zones

The pressure sensitive adhesive zone and the water soluble film zone may be continuous or discontinuous such that they comprise continuous or discontinuous patterns. In an aspect the adhesive zone and the soluble film zone may both be continuous. In some aspects a portion of the adhesive zone and the soluble film-zone are continuous and another portion may be discontinuous. By applying the soluble film zone and the adhesive zone to the backing layer in a discontinuous pattern, a portion of the skin-facing surface of the product and the adhesive zone remains exposed to the skin to permit sufficient adhesion, via the pressure sensitive adhesive, to the skin. In one aspect the soluble film zone should be applied to the adhesive zone so that it covers about 1% to about 99% of the skin facing surface area of the adhesive zone or product, or about 10% to about 90%, and/or about 20% to about 80% of the skin facing surface area of the adhesive zone or the product.

In one aspect the pressure sensitive adhesive zone is applied to the backing layer in a pattern to define a pattern of discontinuous adhesive free areas and the soluble film zone is applied to the adhesive free areas of the backing layer. In another aspect the pressure sensitive adhesive zone is applied to the backing layer in a series of rows or stripes to define a pattern of adjacent adhesive free areas that are stripes or rows, and the soluble film zone is applied to the adhesive free areas/stripes of the backing layer.

The soluble film zone may be applied to the adhesive zone or the backing layer in a regular pattern, a random pattern, and combinations thereof. For example, the soluble film zone may be configured in either a regular or random pattern of elements such as straight lines, angled lines, curved lines, intersecting lines, dots, circles and geometric shapes, amorphous shaped, etc. or a combination of these elements.

Size and Shape of Product

The product may have a size and shape adapted to conform to a desired target area of skin which could be a human face or part thereof, legs, hands, arms, feet, or human torso. They are generally flat in appearance.

The exact size and shape of the product will depend upon the intended use and product characteristics. The product herein can be, for example, a square, circle, semicircle, rectangle, triangle, oval, ring, crescent, crescent with rounded corners, teardrop or other more complex and irregular shape. The shape of the barrier patch may be selected from the group consisting of circle, square, rectangle, triangle, and/or irregular shape that conforms to the contours of the forehead, perioral, and/or periorbital areas of the human face.

In certain other aspects, the product comprises a size and shape to treat different areas of the face such as the forehead, the under eye area and the under eye area combined with the crows feet area around the eye. Thus the size of the product may be determined by the size of the target area of skin to be treated. Thus a product is shaped to fit the face or the target area of skin the surface area may range from about 0.25 cm$^2$ to about 50 cm$^2$, and/or from about 1 cm$^2$ to about 30 cm$^2$, and/or from about 1 cm$^2$ to about 20 cm$^2$, and/or from about 1 cm$^2$ to about 15 cm$^2$, and/or from about 5 cm$^2$ to about 15 cm$^2$. Surface area refers to that of a flat plane having the same boundary as the surface i.e. ignoring any surface texturing present.

WVTR

According to one aspect, the backing layer or barrier patch has an WTVR value between about 1 g/m$^2$/24 h to about 500 g/m$^2$/24 h, and in another aspect has a WVTR from about 1 g/m$^2$/24 h to about 250 g/m$^2$/24 h and/or from about 1 g/m$^2$/24 h to about 1.80 g/m$^2$/24 h and/or from about 2 g/m$^2$/24 h to about 150 g/m$^2$/24 h and/or from about 2 to about 20 g/m$^2$/24 h. The term WTVR stands for "Water Vapor Transmission Rate", i.e. the amount of vapor which can pass per unit area during a certain period of time.

The backing layer or barrier patch in certain aspects is non-porous or water impermeable. In certain other aspects the multi-layered barrier patch or backing layer is impermeable to the cosmetic composition, the soluble film zone, the skin care active agent employed, and fluids wherein the WVTR is from about from about 2 to about 100 g/m$^2$/24 h. While not being bound by theory using a backing layer or barrier patch that minimizes water loss from the soluble film or cosmetic composition while in contact with the keratinous tissue and skin, prevents the water soluble film zone or cosmetic composition, once hydrated, from drying out. This drying out may result in reduced or loss of efficacy and/or irritation to the skin.

Such relative water impermeability and lower water vapor permeability of the barrier patch may increase the effectiveness and efficiency of the cosmetic composition. For example, without being bound by theory, the relative water impermeability and lower vapor permeability of the barrier patch employed may serve to enhance or increase the penetration of the skin care active agent into the skin.

In certain aspects the backing layer or barrier patch may, for example, consist of a perforated polyolefin film, where the size of the holes has been chosen so that air and vapor may pass, but not liquid molecules. One example of such film is described in U.S. Pat. No. 5,628,737 and/or microporous plastic films, as is described in, for example, EP-A-0238200. These laminates and films, however, are not preferred herein due to their relatively high WVTR and higher levels of breathability.

Release Layer

The product herein may further optionally comprise a protective release layer removably attached to the consumer facing side of the pressure sensitive adhesive or the soluble film zone of the product. The release layer provides protection for the pressure sensitive adhesive zone and/or the soluble film zone from the environment and prior to application by the user.

The protective release layer may comprise materials including polymer resins such as a polyolefins e.g. polypropylene (including stratified biaxially oriented polypropylene (SBOPP)), polyethylene (including LDPE; LLDPE; HDPE; Metallocene) or polyethylene terephthalate, polyesters, and combinations thereof. Alternative materials which may be used include polyvinylchloride, polyamide, acetyl, acrylonitrile butadiene styrene, acrylic, acrylonitrile styrene acrylate, ethylene vinyl alcohol, ethylene vinyl acetate, Nylon, Latex, natural or synthetic rubbers, polycarbonate, polystyrene, silicone or thermo plastic elastomer, thermo plastic vulcanate or copolymers of said materials, and combinations thereof. Where appropriate the protective release layer may comprise one or more laminations, combinations of multiple layers. In an aspect the protective release layer may comprise a coating of a non-stick material. Exemplary non-stick coatings include wax, silicone, fluoropolymers such as TEFLON®, and fluorosilicones.

In an aspect, the protective release layer covers the entire aforementioned area of pressure sensitive adhesive zone coating the barrier patch. In another aspect the protective release layer is water impermeable. In a further aspect, the release layer has a mean thickness of at least about 50 microns, or at least about 85 microns, or from about 50 microns to about 150 microns, and/or from about 90 microns to about 120 microns.

The release layer may optionally extend, in whole or part, beyond the pressure sensitive adhesive zone to provide a removal tab that facilitates ease of removal of the release layer.

Cosmetic Composition

Skin Active Agents

In one aspect the product provides an effective amount of a skin active agent to be delivered to the target area of skin. In another aspect the product provides from about 0.5 mg/cm2 to about 3 mg/cm2 of the cosmetic composition, and/or from about 1 mg/cm2 to about 2 mg/cm2 to the target area of skin. In one aspect and without being bound by theory, the use of the proper amount of the cosmetic composition will minimize the interaction of the cosmetic composition with the pressure sensitive adhesive. The compositions of the present invention may comprise a skin active agent which provides a particular skin care benefit characteristic of the usage of the skin care product. The skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, desquamation enzyme enhancers, anti-glycation agents, diaper rash agents, anti-eczema agents, botanicals, and mixtures thereof. When included, the present composition comprises a safe and effective amount of a skin active agent and/or from about 0.0001% to about 20%, in another aspect from about 0.01% to about 10% of at least one skin active agent.

The cosmetic compositions may include from about 0.00001 to about 10% by weight of botanical actives or from about 0.01 to about 8 percent by weight, or from about 0.05 to about 5 percent by weight. "Botanical" herein means a substance, extract or derivative of a plant and may also be described as "herbals". Botanicals may include water-soluble or oil-soluble active materials extracted from a particular plant including materials extracted from echinacea, yucca glauca, willow herb, basil leaves, Turkish oregano, carrot root, grapefruit fruit, fennel fruit, rosemary, thyme, blueberry, bell pepper, black tea, blackberry, black currant fruit, Chinese tea, coffee seed, dandelion root, date palm fruit, gingko leaf, green tea polyphenols (e.g. epicatechin gallate and epigallocatechin 3-O-gallate), hawthorn berries, licorice, oolong tea, sage, strawberry, sweet pea, tomato, vanilla fruit, neohesperidin, quercetin, rutin, morin, myricetin, chlorogenic acid, glutathione, glycyrrhizin, absinthe, arnica, centella asiatica, chamomelle, comfrey, cornflower, horse chestnut, ivy (Herdera helix), magnolia, mimosa, oat extract, pansey, scullcap, seabuckthorn, white nettle, witch hazel and any combinations thereof.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™, available from Seppic Inc.

Skin lightening agents useful herein refer to active ingredients that improve hyperpigmentation as compared to pre-treatment. Useful skin lightening agents herein include ascorbic acid compounds, vitamin $B_3$ compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

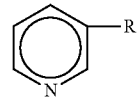

wherein R is —$CONH_2$ (e.g., niacinamide) or —$CH_2OH$ (e.g., nicotinyl alcohol); derivatives thereof; and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and in another aspect is niacinamide. In a preferred aspect, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably substantially free of the salt form. Commercially available vitamin $B_3$ compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example available from Roche Vitamins), ascorbyl dipalmitate (for example, NIKKOL CP available from Nikko Chemical); undecylenoyl phenyl alanine (for example, SEPIWHITE MSH available from Seppic); octadecenedioic acid (for example, ARLATONE DIOIC DCA available from Uniquema); oenothera biennis sead extract, and pyrus malus (apple) fruit extract, Water and Myritol 318 and butylene glycol and tocopherol and sscorbil tetraisopalmitate and Paraben and Carbopol 980 and DNA/SMARTVECTOR UV available from COLETICA, magnesium ascorbyl phosphate in hyaluronic filling sphere available from COLETICA, and mixtures thereof.

Other skin active agents useful herein include those selected from the group consisting of N-acetyl D-glucosamine, panthenol (e.g., DL panthenol available from Alps Pharmaceutical Inc.), tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutarioic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate: DL-α-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

The compositions of the present invention in various aspects may comprise N-acyl amino acid compounds. Suitable N-acyl amino acid compounds include, but are not limited to, N-acyl phenylalanine, N-acyl tyrosine, their isomers, including their D and L isomers, salts, derivatives, and mixtures thereof. An example of a suitable N-acyl amino acid is N-undecylenoyl-L-phenylalanine is commercially available under the tradenanie SEPIWHITE (Registered trademark) from Seppic (France).

Skin care agents are also disclosed in US Publication No. 2007/0020220A1, published Jan. 25, 2007, wherein the components/ingredients are incorporated herein by reference in their entirety.

The cosmetic composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide also refers to both naturally occurring and synthesized peptides. In one aspect, the peptides are di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and palmitoyl-lysine-threonine-threonine-lysine-serine (pal-KTTKS, available in a composition known as MATRIXYL®) palmitoyl-glycine-glutamine-proline-arginine (pal-GQPR, available in a composition known as RIGIN®), these three being available from Sederma, France, and Cu-histidine-glycine-glycine (Cu-HUG, also known as IAMIN®). In various aspects the cosmetic composition may comprise from about $1 \times 10^{-7}$% to about 20%, alternatively from about $1 \times 10^{-6}$% to about 10%, and alternatively from about $1 \times 10^{-5}$% to about 5% of the peptide.

In one aspect, the skin active agent is niacinamide. In one aspect, the agent is a combination of niacinamide, glycerine, tocopherol acetate, and D-panthenol. Niacinamide may be included in the composition in an amount between about 1% to about 30 wt %, in another aspect from about 2% to about 28 wt %, in another aspect from about 5% to about 25 wt %, and in another aspect from about 10% to about 20 wt %. When D-panthenol is included, it may be present in an amount of about 0.5% to about 5 wt %, or about 0.5% to about 3 wt % and/or about 0.5% to about 2 wt %. Glycerin may be included as an active in an amount from about 6% to about 20 wt %, and/or from about 8% to about 15 wt %, and/or from about 10% to about 15 wt %.

In various aspects, the skin active agent is selected from niacinamide, alone or in combination with one or more of palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, and combinations thereof.

In an aspect the cosmetic compositions herein may be aqueous solutions, or emulsions such as oil-in-water emulsions, water-in-oil emulsions or multiple emulsions having aqueous or oily external phases. In another aspect the cosmetic compositions herein are oil-in-water emulsions.

In one aspect to avoid a negative interaction with the pressure sensitive adhesive, the cosmetic composition or water soluble film zone comprises only low levels of silicones of about 0.5% to about 10%, and/or from about 1% to about 5% and/or the cosmetic composition is substantially free of silicones. As used herein "silicones" may refer to those silicones disclosed in US 2007/0020220A1, published Jan. 25, 2007, Osborne, for example in paragraphs [0226] to [0258].

In one aspect the cosmetic composition is substantially free of depilatory agents.

The cosmetic composition or water soluble film zone may comprise an effective amount of a skin active agent having activity to improve visual or aesthetic appearance of the skin, such as an agent effective to reduce or diminish the appearance of fine lines and/or wrinkles on human facial skin or an agent effective to treating existing acne lesions, reducing redness associated with acne lesions and/or protecting from formation of acne lesions.

In another aspect a method of treating skin is provided, comprising applying the product to a target area of the skin, comprising an effective amount of a skin active agent.

The methods of treatment, application, regulation, or improvement disclosed herein may utilize the aforementioned product and/or multi-layered barrier patch. Application of the present product can occur on any target area of skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, application may be on a facial skin surface including the forehead, perioral, chin, periorbital, nose, and/or cheek skin surfaces.

The step of applying the product to a target area of skin may be done by localized application to the target area, for example an area that contains wrinkles. In reference to the application, the term "localized", "local", or "locally" mean that it is delivered to the target area of skin (such as an area of skin containing wrinkles) while minimizing delivery to skin surface not requiring treatment.

One or more products of the present invention can be applied broadly to one or more facial skin surfaces to reduce the appearance of wrinkles within those facial skin regions.

The method of treating skin herein may optionally begin with a cleansing step. The consumer can wash his or her face with a suitable cleanser (e.g., Olay Purifying Mud Lathering Cleanser, available from The Procter & Gamble Company, Cincinnati, Ohio), and gently dry his or her skin.

The product may be applied to at least one target portion of skin selected from the group consisting of a forehead, perioral, chin, periorbital, nose, cheek, skin surface, and combinations thereof. The product may be applied to the target portion of skin for a treatment period. The treatment period may comprise at least once a day for at least four weeks, preferably applied at least twice a day for at least four weeks, more preferably at least once a day for at least eight weeks, and more preferably at least twice a day for at least eight weeks, preferably the length of the treatment period is at least 2 weeks, preferably at least 4 weeks, and more preferably at least 8 weeks. The product may remain on the target portion of skin for about 1 minute to about 24 hours or from about 2 hours to about 10 hours, prior to the removal from the skin. In an aspect the target portion of skin comprises a hyperpigmented spot, wrinkles, fine lines, dryness, skin laxity and combinations thereof.

Test Methods

Tensile/Modulus Test Method

Tensile (modulus) properties are measured on a constant rate of extension tensile tester with computer interface (a suitable instrument is the MTS Insight using Testworks 4.0 Software, as available from MTS Systems Corp., Eden Prairie, Minn.) using a load cell for which the forces measured are within 1% to 99% of the limit of the cell. Both the movable (upper) and stationary (lower) fixture are fitted with light weight vise action grips, wider than the width of the test specimen. The tensile tester is fitted with a specimen humidity and temperature control chamber that can maintain the specimen's environment at a set temperature between 23° C. and 40° C. with an accuracy of ±0.5° C. and at a set relative humidity of between 35% and 95% with an accuracy of ±0.5% throughout the tensile experiment. All testing is performed in a conditioned room maintained at about 23° C.±2° C. and about 50±2% relative humidity.

Program the tensile tester for an extension test after performing an initial gage length adjustment. To perform the gage length adjustment, first lower the crosshead 5.0 mm at a rate of at 7.5 mm/s to add slack to the specimen. Then raise the crosshead at 7.5 mm/s until 0.1 N is measured at the load cell, and set the current gage at this point as the adjusted gage length. Continue to raise the crosshead at 7.5 mm/s until the specimen breaks, i.e., that the force drops to <0.05 N after the maximum peak force. Force and crosshead travel data are collected at 200 Hz throughout the experiment. Return the crosshead to the original gage length.

Samples are conditioned at about 23° C.±2° C. and about 50%±2% relative humidity for at least two hours before testing. Determine the machine direction (MD) and cross direction (CD) of the samples. Using a JDC cutter (available from Thwing-Albert) or other appropriate means, cut eighteen (18) specimens 80 mm long by 25.4±0.1 mm wide in the cross direction. Next cut eighteen (18) specimens 80 mm long by 25.4±0.1 mm wide in the machine direction. Measure the caliper of each specimen using a digital linear caliper (e.g. an Ono Sokki GS-503 or equivalent) fitted with a 25 mm diameter foot that applies a pressure of 0.69 kPa. Zero the caliper foot against the anvil base. Lift the foot and place the specimen flat against the anvil base, with the specimen width centered beneath the pressure foot, and lower the foot at about 5 mm/sec onto the specimen avoiding any creases, folds, or obvious defects. Read the caliper (mm) 5.0 sec after resting the foot on the specimen and record to the nearest 0.01 mm. Calculate the cross sectional area of each specimen as the width of the specimen multiplied by the caliper, and record to 0.01 mm$^2$.

Accurately set the initial gage length to 75.0 mm and zero the crosshead and load cell. Insert the specimen into the upper grips, aligning it vertically within the upper and lower grips, close the upper grip and tighten. Insert the opposite end of the specimen into the lower grip and tighten. The specimen should have minimal slack with less than 0.1 N force measured at the load cell. Seal the environmental chamber and allow the temperature and humidity to reach the set target values, and then maintain these conditions for 10 minutes prior to testing. Start the test program.

Plot the Force (N) versus Extension (mm) curve. Herein Extension is the travel length corrected for the adjusted gage length. Read and record the maximum Peak Force and report to the nearest 0.1 N. Calculate the Energy to Break as the area under the curve between the start of extension to the final extension at break. Record to the nearest 0.01 N*mm.

Using the force (N) and extension data (mm), construct an engineering Stress (MPa) versus engineering Strain curve. Herein engineering stress s is defined as force (N) divided by the initial cross sectional area (mm$^2$) of the specimen. Engineering strain e is the change in length (from the adjusted gage length) divided by the adjusted gage length. From the curve read the Failure Stress (MPa) as the maximum stress of the curve and record to the nearest 0.01 MPa. From the curve calculate the Modulus (MPa) as the greatest slope of a linear segment of the curve, prior to the 10% strain, wherein the length of the segment incorporates 0.01 mm/mm strain increment. Record to the nearest 0.01 MPa.

The analysis is performed for three replicate CD and three replicate MD specimens, at each of the following target environmental conditions:

|   | Temperature (° C.) | Relative Humidity (%) |
|---|---|---|
| 1 | 25 | 40 |
| 2 | 25 | 75 |
| 3 | 25 | 90 |
| 4 | 37 | 40 |
| 5 | 37 | 75 |
| 6 | 37 | 90 |

Calculate the arithmetic mean for the three replicate CD results at each environmental condition. Separately calculate the arithmetic mean for the three replicate MD results at each environmental condition, report Modulus to the nearest 0.1 MPa, Failure Stress to the nearest 0.1 MPa, Peak Force to the nearest 0.01 N and Energy to Break to the nearest 0.1 N*mm for each of the environmental conditions. Initial Modulus is determined as the modulus at 40% RH at 25° C. Calculate the Modulus drop/decrease by comparing 75% RH at 37° C. to the 40% RH at 25° C. or by comparing 90% RH at 37° C. to 40% RH at 25° C.

$$\text{Modulus Decrease} = \frac{\text{Initial Modulus} - \text{Final Modulus}}{\text{Initial Modulus}} \times 100$$

Percentage Weight Gain

In an aspect, once the soluble film zone or product is exposed to a low water environment and/or is occluded on the skin as described herein (e.g. by using a backing layer with the requisite low WVTR), it has a weight change. The following method is used to quantify this change in weight. To approximate the change in weight for the water soluble film zone, the water soluble film made from the water soluble film forming polymer may also be used in the method.

Provide 12, 4 oz glass jars with screw caps containing a grid tray on the bottom and a weigh boat that is suspended on the grid tray. Label the jars Nos. 1 through 12. Provide a saturated aqueous solution of potassium chloride below the weigh boat to create a chamber humidity of 85% at ambient conditions. Cut ¾"×¾" samples of a film/product. Then add a sample into each of the jars and into the weigh boats. Weight each of the weigh boats with the samples in the boat. This is the initial weight.

Start the time count after adding the samples to the jar, starting with the #1 jar. At specific time intervals outlined below, remove the sample and weigh boat from the designated jar (starting with #1) and weigh the sample and weigh boat together. This is the subsequent weight. Then calculate the % weight gain.

$$\% \text{ weight increase} = \frac{\text{subsequent weight} - \text{initial weight}}{\text{initial weight}} \times 100$$

Sample #/Time intervals:
1/10 min
2/20 min
3/30 min
4/40 min
5/50 min
6/1 h

7/2 h
8/3 h
9/4 h
10/5 h
11/6 h
12/24 h
Measure each of the samples 3 times and then average. Record the average values for 1 hour, 6 hours, and 24 hours for the sample.

WVTR

WVTR of the barrier patch or backing layer is measured according to ASTM F1249 13 at 37° C. and 35% RH. Samples may be analyzed on a MOCON Permatran-W 3/33 Water Vapor Permeability Instrument using ASTM F1249. For samples with higher WVTR (e.g. from approximately 300 g/m$^2$/24 h to 500 g/m$^2$/24 h) samples may be analyzed per ASTM E-96 with desiccant placed inside the test cups and 35% RH surrounding the exterior of the cups. Samples of barrier patches are prepared and do not include the pressure sensitive adhesive.

Basis Weight

Basis Weight is calculated as follows. Sample Preparation: Samples were equilibrated at TAPPI conditions for 100 hours (50% RH, 23° C.). Cut samples to 25.4 mm wide strips using JDC 1" strip cutter. Cut samples to 80 mm long using gage block. Weigh each sample using 4 place analytical balance. Basis weight is calculated as the sample mass/area, where mass is measured on the balance and area=25.4 mm×80 mm=2032 mm=0.002032 meters. Basis weight is reported in units of grams/meter$^2$.

Caliper/Thickness

Thickness measurement may be performed using ASTM D5729 which typically uses a pad caliper with a known pressure (0.1 psi) and a gage sensor. A Qualitest Thickness Tester, Model CHY-C2, available from www.WorldofTest.com may be used.

Dissolution Method

The water soluble film is aged for 24 hours at 21° C. (+/−1.5° C.) and 50% relative humidity (+1-1.5% relative humidity). Cut three test specimens of the water-soluble film sample to a size of 3.8 cm×3.2 cm. Lock each specimen in a separate 35 mm slide mount. Fill a suitable beaker with 500 mL of distilled water, and maintain a constant temperature of 20° C. Mark height of column of water. Place beaker on magnetic stirrer, add magnetic stirring rod to beaker, turn on stirrer, and adjust stir speed until a vortex develops which is approximately one-fifth the height of the water column. Mark depth of vortex. Secure the 35 mm slide mount in an alligator clamp of a slide mount holder such that the long end of the slide mount is parallel to the water surface. The depth adjuster of the holder should be set so that when dropped, the end of the clamp will be 0.6 cm below the surface of the water. One of the short sides of the slide mount should be next to the side of the beaker with the other positioned directly over the center of the stirring rod such that the film surface is perpendicular to the flow of the water. In one motion, drop the secured slide and clamp into the water and start the timer. When all visible film is released from the slide mount, raise the slide out of the water while continuing to monitor the solution for undissolved film fragments. For each sample, record the time when all film fragments of each sample are no longer visible to the naked eye, and the solution becomes clear. Average the time values for the 3 samples and if the average time is 15 minutes or less, then the sample constitutes a water soluble film.

EXAMPLES

The following are non-limiting examples of products and methods of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

A. Preparation of Beauty Care Product:

The following formulation and procedure is used:

|  | Component | Weight % |
| --- | --- | --- |
| Solution A | PEG 100 Stearate (surfactant) | 1% |
|  | Emulgade PL 68-50[1] (surfactant) | 1% |
|  | Eutanol G 16[2] (hexyldecanol) | 10% |
| Solution B | Sepiwhite MSH (Undecylenoyl phenylalanine)[3] | 0.4% |
|  | 1N Sodium Hydroxide solution | 1.26% |
| Solution C | Water | 52.34% |
|  | Niaciniamide | 10% |
|  | Glycerol | 20% |
|  | Inositol | 4% |

[1]Available from BASF.
[2]Available from BASF.
[3]Available from BASF.

Mix the ingredients of Solution A and heat to 80° C. with stirring. Then place Solution B ingredients into a small beaker and stir until the solution becomes clear to deprotonate the Sepiwhite MSH to make it soluble in water. Then heat ingredients of Solution C to 80° C. with stirring.

Add Solution B slowly to Solution C with rapid stirring for 10 minutes. Then add Solution A slowly over 15 minutes with rapid stirring at 80° C. and stir for 30 minutes and then mill with a hand held mill for 2 minutes at 80° C. Stir the solution and allow to cool to RT. Once at RT, place the solution into a jar and label. After 96 hours, the solution is stable with no separation and no solids forming.

Once the above emulsions are obtained, mix a 60:40 ratio (of polymer solution to emulsion) of the water-soluble polymer solution of Methocel E5LV at a 20% solution in water, with the emulsion. Then cast a film with the use of a Gardo Draw Down table and a #44 Draw Down bar, onto a transfer sheet. Methocel E5LV is a water soluble cellulose ether of low viscosity available from Dow/Coloron LTD.

Backing and Adhesive Layer

A backing layer according to Sample 3 of Provisional US Patent Application Ser. No. 62/257,341, filed on Nov. 19, 2015, is provided. In particular Sample 3 is a 3 layer film having a foamed core layer and non-foamed outer layers. All layers are made of EVA. The outside layers each have approximately 20 μm thickness and the core foamed layer has approximately 130 μm thickness. The total thickness of the backing layer is approximately 170 μm. The basis weight is about 99 gsm and the WVTR is 82 g/m$^2$/24 hours. The backing layer has a first surface. Alternatively the backing layer may comprise a low density polyethylene film or a non-foamed laminate of EVA. The backing layer or barrier patch may also comprise a polyethylene film sold under the tradename, 3M 1525L, available from 3M, St. Paul, Minn., (without the release layer) which has a hacking of polyethylene film of approximately 3 mil thickness and a 1.4 mil thick hypoallergenic, pressure sensitive acrylate adhesive layer.

Slot coat a pressure sensitive adhesive (if an adhesive is not already present with the backing layer), such as for example, TECHNOMELT® and DERMA-TAK® brands available from Henkel, (for example TECHNOMELT PSM 154A DERMA-TAK®) at a basis weight of about 50 g/m² to about 160 g/m² or specifically about 95 g/m², on the first surface of the backing layer. Slot coat the pressure sensitive adhesive as a continuous layer across the first surface of the backing layer.

After the coating of pressure sensitive adhesive is complete, the upper surface of the pressure sensitive adhesive layer/zone is coated with the above soluble film comprising the skin active agent by contacting the soluble film side of the transfer sheet to the upper surface of pressure sensitive adhesive. The soluble film is coated as a discontinuous layer on the upper (outer) surface of the pressure sensitive adhesive layer/zone. The soluble film has a coating basis weight from about 30 g/m² to about 200 g/m².

The assembly of the barrier patch may also be accomplished by the methods described in U.S. Ser. Nos. 62/257,341; 62/257,347 and 62/257,351, assignee Procter & Gamble, each filed on Nov. 19, 2015.

Exemplary products, for example the Product of the above example, for treatment of periorbital skin aging are attached, via the adhesive side, to periorbital area. The Product is applied and worn for an extended period of time of approximately 7-8 hours such as overnight, and thereafter removed. The Products herein deliver an effective amount of the skin active agent in a manner that achieves penetration of the skin active agent into the stratum corneum, and/or other layers of the epidermis, and in many aspects, into the basal skin layer and/or dermis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance of skin comprising the steps of:
   identifying a target portion of skin; and
   topically applying, to the target portion of skin, a multi-layered beauty care product for a treatment period, the multi-layered beauty care product comprising:
   a barrier patch comprising:
      a backing layer comprising one or more layers of ethylene vinyl acetate and having a first surface and a second surface; a water vapor transmission rate (WVTR) of about 1 g/m²/24 h to about 500 g/m²/24 h;
      a pressure sensitive adhesive layer, having an upper surface and a lower surface, the lower surface of the pressure sensitive adhesive layer in contact with the first surface of the backing layer; and
      a discontinuous water soluble film layer comprising a plurality of discrete water soluble film zones spatially separated from one another by the pressure sensitive adhesive layer, wherein each of the water soluble film zone comprises
      a water soluble film forming polymer;
      a cosmetic composition comprising an effective amount of a skin active agent; and
      about 2% to about 80% by weight of a plasticizer selected from the group consisting of glycerol, ethylene glycol, diethyleneglycol, propylene glycol, sorbitol, pentaerythritol, glucamine, N-methylglucamine, sodium cumenesulfonate, and combinations thereof;
      wherein the water soluble film layer is in contact with either the first surface of the backing layer, the upper surface of the pressure sensitive adhesive layer, or both; and
      wherein the water soluble film layer has an initial modulus of from about 30 MPa to about 600 MPa and the water soluble film is capable of a modulus reduction of about 90% to about 100% at 37 C and 75% relative humidity compared to the initial modulus at 25 C and 40% relative humidity, wherein the water soluble film layer or product comprises a % weight increase, at 1 hour, 6 hours or 24 hours, of about 20 to about 80%.

2. The method of claim 1 wherein the initial modulus is from about 75 MPa to about 500 MPa.

3. The method of claim 1 wherein the water soluble film layer or product comprises a modulus reduction of about 90% to about 100% compared to the initial modulus.

4. The method of claim 1 wherein the WVTR is from about 1 g/m²/24 h to about 250 g/m²/24 h.

5. The method of claim 1 wherein the water soluble film layer comprises from about 30% to about 99%, of the water soluble film forming polymer selected from the group consisting of polyethylene oxide polymer, polyvinyl alcohols, polyvinyl alcohol copolymers, starch, methylcellulose, carboxymethylcellulose sodium, hydroxyethyl cellulose, hydroxypropyl methylcellulose and combinations thereof.

6. The method of claim 5 wherein the water soluble film forming polymer comprises methylcellulose, hydroxypropyl methylcellulose, polyethylene oxide or combinations thereof.

7. The method of claim 5 wherein the water soluble film forming polymer is polyethylene oxide having a molecular weight from about 500 to about 10,000,000.

8. The method of claim 7 wherein the molecular weight of the polyethylene oxide is from about 100,000 to about 300,000.

9. The method of claim 1, wherein the backing layer comprises a modulus reduction of about 25% to about 50% when conditions change from 25° C./40% RH to 37° C./90% RH.

10. The method of claim 1 further comprising a ratio of the modulus of the water soluble film layer to the modulus of the backing layer or barrier patch, wherein the modulus ratio is greater than 1 at 25° C./40% RH and the ratio is less than 1 at 37° C./90% RH.

11. The method of claim 1 wherein the water soluble film layer further comprises a top surface and a bottom surface.

12. The method of claim 11 wherein the bottom surface of the water soluble film layer is in contact with the upper surface of the pressure sensitive adhesive layer and the pressure sensitive adhesive layer is continuous.

13. The method of claim 11 wherein the top surface of the water soluble film layer and the upper surface of the pressure sensitive adhesive layer are co-planar or collinear.

14. The method of claim 11 wherein the bottom surface of the water soluble film layer and the lower surface of the pressure sensitive adhesive layer are co-planar or collinear.

15. The method of claim 1 wherein the barrier patch or backing layer is water impermeable.

16. The method of claim 1 wherein the water soluble film has a total thickness of about 2 microns to about 150 microns.

17. The method of claim 1 wherein the barrier patch or product has a total thickness of 20 microns to 500 microns.

18. The method of claim 1 wherein the product, barrier patch, or backing layer is substantially free of fibrous absorbent materials, superabsorbent materials, non-woven materials, cotton, rayon, acrylics, polypropylene fibers or polyester fibers.

19. The method of claim 1 wherein the pressure sensitive adhesive layer is selected from the group consisting of acrylic and methacrylic ester homo- or copolymers, butyl rubber based systems, silicones, urethanes, vinyl esters and amides, olefin copolymer materials, and combinations thereof.

20. The method of claim 1 wherein the backing layer is substantially free of an effective amount of the skin agent.

21. The method of claim 1 wherein the backing layer is a laminate comprising a film and a non-woven material.

22. The method of claim 1 wherein the target portion of skin is healthy skin.

23. The method of claim 1 wherein the target portion of skin is selected from the group consisting of forehead skin, perioral skin, chin, periorbital skin, nose, cheek, skin surface, and combinations thereof and is also selected from the group consisting of a hyperpigmented spot, wrinkles, fine lines, dryness, skin laxity and combinations thereof.

24. The method of claim 1 wherein the treatment period comprises application to the skin once or twice a day for at least two weeks or at least eight weeks and the product remains on the target portion of skin for about 1 minute to about 24 hours prior to the removal from the skin.

* * * * *